United States Patent
Jia et al.

(10) Patent No.: US 11,306,085 B2
(45) Date of Patent: Apr. 19, 2022

(54) METHOD FOR PREPARING PYRIMIDONE HETEROARYL DERIVATIVE AND INTERMEDIATE OF PYRIMIDONE HETEROARYL DERIVATIVE

(71) Applicant: Jiangsu Hengrui Medicine Co., Ltd., Jiangsu (CN)

(72) Inventors: Junlei Jia, Jiangsu (CN); Bing Liu, Jiangsu (CN); Xiaohui Gao, Jiangsu (CN)

(73) Assignee: Jiangsu Hengrui Medicine Co., Ltd., Jiangsu (CN)

( * ) Notice: Subject to any disclaimer, the term of this patent is extended or adjusted under 35 U.S.C. 154(b) by 0 days.

(21) Appl. No.: 16/632,698

(22) PCT Filed: Jul. 27, 2018

(86) PCT No.: PCT/CN2018/097365
§ 371 (c)(1),
(2) Date: Jan. 21, 2020

(87) PCT Pub. No.: WO2019/020102
PCT Pub. Date: Jan. 31, 2019

(65) Prior Publication Data
US 2020/0140434 A1     May 7, 2020

(30) Foreign Application Priority Data

Jul. 28, 2017 (CN) .......................... 201710631867.0

(51) Int. Cl.
C07D 487/04 (2006.01)
C07D 471/04 (2006.01)
C07D 495/04 (2006.01)

(52) U.S. Cl.
CPC ......... *C07D 471/04* (2013.01); *C07D 487/04* (2013.01); *C07D 495/04* (2013.01)

(58) Field of Classification Search
CPC .................................................. C07D 487/04
See application file for complete search history.

(56) References Cited

FOREIGN PATENT DOCUMENTS

| WO | 2011/090935 A1 | 7/2011 |
| WO | 2013/071169 A1 | 5/2013 |
| WO | 2013071169 A1 | 5/2013 |
| WO | 2013/129879 A1 | 9/2013 |
| WO | 2013129879 A1 | 9/2013 |
| WO | 2015/062391 A1 | 5/2015 |
| WO | 2015062391 A1 | 5/2015 |

OTHER PUBLICATIONS

International Search Report dated Nov. 1, 2018 in International Application No. PCT/CN2018/097365.
Written Opinion dated Nov. 1, 2018 in International Application No. PCT/CN2018/097365.
Samant, Manoj P., et al., "Novel Analogues of Degarelix Incorporation Hydroxy-, Methoxy-, and Pegylated-Urea Moieties at Positions 3, 5, 6 and the N-Terminus. Part III," J. Med. Chem., vol. 49, pp. 3536-3543, May 23, 2006.
Extended European Search Report dated Dec. 1, 2020 in corresponding European Application No. 18837896.2.
Int'l Search Report dated Nov. 1, 2018 in Int'l Application No. PCT/CN2018/097365.

*Primary Examiner* — Brian E McDowell
(74) *Attorney, Agent, or Firm* — Ice Miller LLP

(57) ABSTRACT

The present invention relates to a method for preparing a pyrimidone heteroaryl derivative and an intermediate of the pyrimidone heteroaryl derivative. Specifically, the pyrimidone heteroaryl derivative of the formula

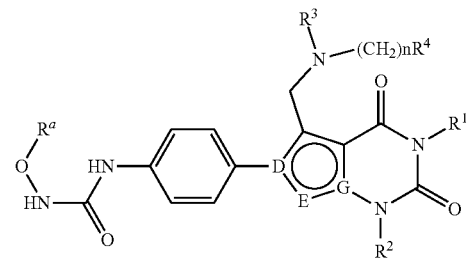

is prepared by changing a starting raw material and an intermediate.

7 Claims, No Drawings

METHOD FOR PREPARING PYRIMIDONE HETEROARYL DERIVATIVE AND INTERMEDIATE OF PYRIMIDONE HETEROARYL DERIVATIVE

CROSS REFERENCE TO RELATED APPLICATIONS

This application is a Section 371 of International Application No. PCT/CN2018/097365, filed Jul. 27, 2018, which was published in the Chinese language on Jan. 31, 2019 under International Publication No. WO 2019/020102 A1, which claims priority under 35 U.S.C. § 119(b) to Chinese Application No. 201710631867.0, filed on Jul. 28, 2017, the disclosures of all of which are incorporated herein by reference in their entireties.

FIELD OF THE INVENTION

The present invention relates to a method for preparing a pyrimidone heteroaryl derivative, and an intermediate for preparing a pyrimidone heteroaryl derivative.

BACKGROUND OF THE INVENTION

Endometriosis is a common estrogen-dependent gynecological disease, which often occurs in women of childbearing age, though the action mechanism of which is unclear. The difficult diagnosis and unclear pathogenesis of endometriosis severely hinder the discovery of effective treatments. At present, endometriosis is mainly diagnosed by laparoscopy, and treated by surgery, or controlled by taking contraceptives, GnRH receptor agonists or progestogen to reduce estrogen levels in the body.

Gonadotropin releasing hormone (Gonadoliberin; GnRH), also known as luteinizing hormone releasing hormone (LHRH), is a decapeptide hormone (pGlu-His-Trp-Ser-Tyr-Gly-Leu-Arg-Pro-Gly-NH2) synthesized by hypothalamic neuroendocrine cells, and is a central regulatory factor of the endocrine and reproductive systems. GnRH plays an important role in the hypothalamus-pituitary-gonadal axis system by being transported to the pituitary through the hypothalamic pituitary portal circulation system and then binding to GnRH receptor cells in the anterior pituitary, by promoting the secretion and release of gonadotropin hormones, such as luteinizing hormone (LH) and follicle-stimulating hormone (FSH), and by regulating normal development of the ovary and corpus luteum. The GnRH receptor plays its regulatory role by coupling with a G protein that can activate the second messenger system of calcium phosphatidylinositol. LH regulates the production of sex steroids, while FSH regulates male spermatogenesis and female follicular development.

WO2015062391A1 (publication date: 7 May 2015) discloses a class of small molecule GnRH receptor antagonists useful in treating endometriosis, uterine fibroids and prostate cancer, and its chemical name is 1-(4-(7-(2,6-difluorobenzyl)-3-((dimethylamino)methyl)-5-(6-methoxypyridazin-3-yl)-4,6-dioxo-4,5,6,7-tetrahydro-2H-pyrazolo[3,4-d]pyrimidin-2-yl)phenyl)-3-methoxyurea. This compound has good activity and can effectively treat the endocrine and reproductive system diseases, and its structure is shown in formula (I-1),

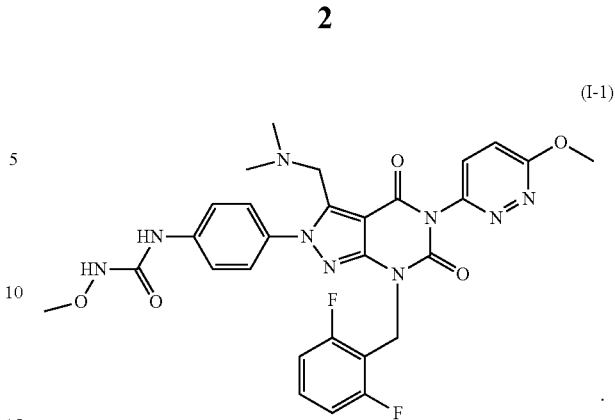

Example 11 of WO2015062391A1 discloses a method for preparing the compound of formula (I-1) in a total of five steps, and the specific reactions are as follows:

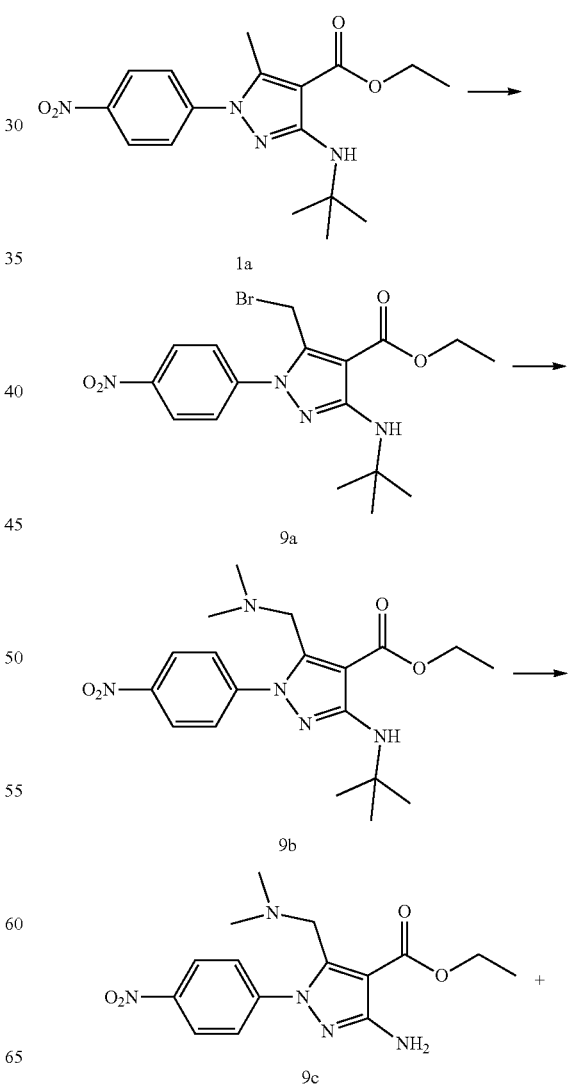

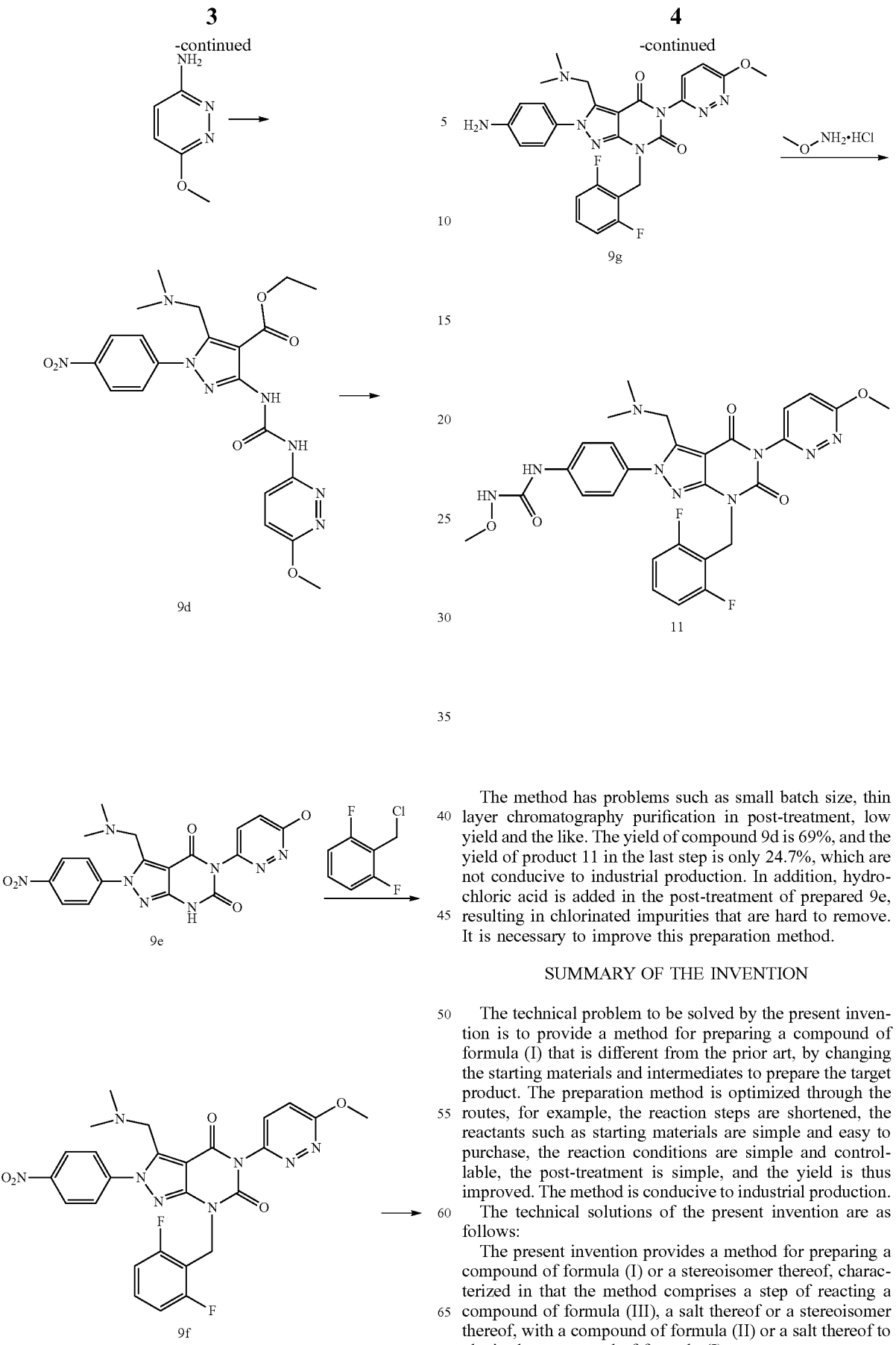

The method has problems such as small batch size, thin layer chromatography purification in post-treatment, low yield and the like. The yield of compound 9d is 69%, and the yield of product 11 in the last step is only 24.7%, which are not conducive to industrial production. In addition, hydrochloric acid is added in the post-treatment of prepared 9e, resulting in chlorinated impurities that are hard to remove. It is necessary to improve this preparation method.

SUMMARY OF THE INVENTION

The technical problem to be solved by the present invention is to provide a method for preparing a compound of formula (I) that is different from the prior art, by changing the starting materials and intermediates to prepare the target product. The preparation method is optimized through the routes, for example, the reaction steps are shortened, the reactants such as starting materials are simple and easy to purchase, the reaction conditions are simple and controllable, the post-treatment is simple, and the yield is thus improved. The method is conducive to industrial production.

The technical solutions of the present invention are as follows:

The present invention provides a method for preparing a compound of formula (I) or a stereoisomer thereof, characterized in that the method comprises a step of reacting a compound of formula (III), a salt thereof or a stereoisomer thereof, with a compound of formula (II) or a salt thereof to obtain the compound of formula (I):

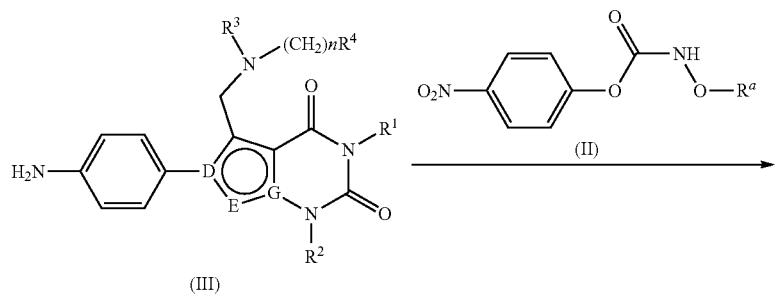

(III)   (II)

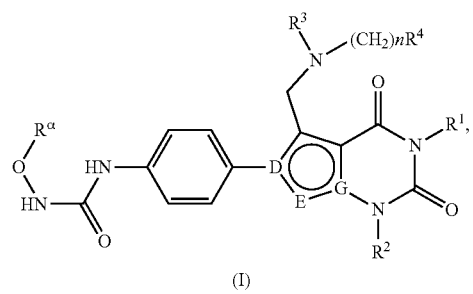

(I)

wherein,
when G is N, D is C, and E is —CH—;
when G is C, D and E are N, or D is C and E is S;

$R^1$ is selected from the group consisting of alkyl, cycloalkyl, heterocyclyl, aryl, heteroaryl and —$OR^5$, wherein the alkyl, cycloalkyl, heterocyclyl, aryl and heteroaryl are each independently and optionally further substituted by one or more substituents selected from the group consisting of halogen, cyano, nitro, alkyl, haloalkyl, hydroxyalkyl, alkenyl, alkynyl, cycloalkyl, heterocyclyl, aryl, heteroaryl, —$OR^5$, —$C(O)OR^5$, —$OC(O)R^5$, —$NHS(O)_mR^5$, —$C(O)R^5$, —$NHC(O)R^5$, —$NHC(O)OR^5$, —$NR^6R^7$, —$OC(O)NR^6R^7$, —$C(O)NR^6R^7$, —$NHC(O)NHR^5$ and —$NHC(O)NHOR^5$;

$R^2$ is alkyl, wherein the alkyl is further substituted by one or more substituents selected from the group consisting of aryl and heteroaryl, wherein the aryl and heteroaryl are optionally further substituted by one or more substituents selected from the group consisting of halogen, alkyl, haloalkyl, cyano, nitro, —$C(O)OR^5$, —$C(O)NR^6R^7$, —$OC(O)NR^6R^7$, —$OR^5$, —$NHS(O)_mR^5$, —$NHC(O)R^5$ and —$NR^6R^7$, wherein the haloalkyl is preferably trifluoromethyl;

$R^3$ is alkyl;

$R^4$ is selected from the group consisting of hydrogen, cycloalkyl, heterocyclyl, aryl, heteroaryl, —$OR^5$, —$NR^6R^7$ and —$NR^6S(O)_mR^5$, wherein the alkyl, cycloalkyl, heterocyclyl, aryl and heteroaryl are optionally further substituted by one or more substituents selected from the group consisting of halogen, oxo, alkyl, haloalkyl, hydroxyalkyl, —$OR^5$, —$C(O)OR^5$, —$OC(O)R^5$, —$NR^7S(O)_mR^5$, —$S(O)_mR^5$, —$C(O)R^5$ and —$NHC(O)R^5$;

$R^5$ is selected from the group consisting of hydrogen, alkyl, cycloalkyl, heterocyclyl, aryl and heteroaryl, wherein the alkyl, cycloalkyl, heterocyclyl, aryl and heteroaryl are each independently and optionally further substituted by one or more substituents selected from the group consisting of alkyl, halogen, hydroxy, alkoxy, haloalkoxy, cycloalkyl, heterocyclyl, aryl, heteroaryl, carboxy and alkoxycarbonyl;

$R^6$ and $R^7$ are each independently selected from the group consisting of hydrogen, alkyl, cycloalkyl, heterocyclyl, aryl and heteroaryl, wherein the alkyl, cycloalkyl, heterocyclyl, aryl and heteroaryl are each independently and optionally further substituted by one or more substituents selected from the group consisting of alkyl, halogen, hydroxy, alkoxy, haloalkoxy, cycloalkyl, heterocyclyl, aryl, heteroaryl, carboxy and alkoxycarbonyl;

or, $R^6$ and $R^7$ together with the nitrogen atom to which they are attached form a heterocyclyl, wherein the heterocyclyl contains one or more heteroatoms selected from the group consisting of N, O and $S(O)_m$, and the heterocyclyl is optionally further substituted by one or more substituents selected from the group consisting of alkyl, halogen, hydroxy, alkoxy, haloalkoxy, cycloalkyl, heterocyclyl, aryl, heteroaryl, carboxy and alkoxycarbonyl;

$R^a$ is alkyl, wherein the alkyl is optionally further substituted by one or more substituents selected from the group consisting of alkyl, halogen, hydroxy, alkoxy, cycloalkyl, heterocyclyl, aryl, heteroaryl, carboxy and alkoxycarbonyl;

m is 0, 1 or 2; and n is 1, 2, 3 or 4.

In the above scheme, the method also comprises the steps of:

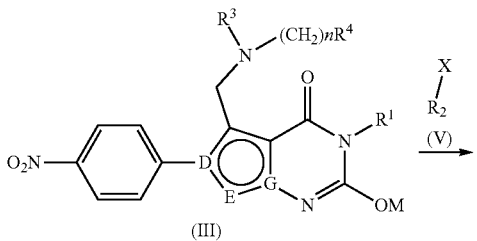

(III)   (V)

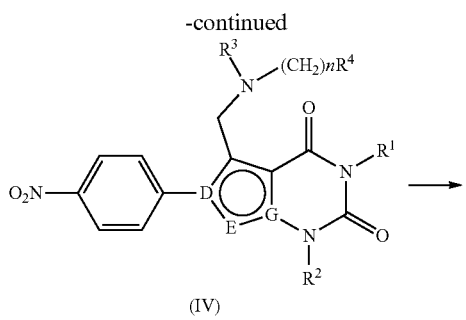

(IV)

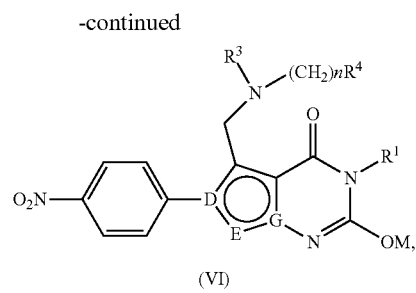

(VI)

wherein, n, D, E, G R$^1$, R$^3$, and R$^4$ are as defined in formula (I);

R$^b$ is alkyl;

the compound of formula (VI) is a mono-metal alkoxide or a bi-metal alkoxide, and M is selected from the group consisting of a monovalent metal cation, a divalent metal cation, a trivalent metal cation and a tetravalent metal cation, preferably a sodium ion, a potassium ion, a lithium ion, a calcium ion, a magnesium ion, a barium ion, an aluminum ion, a copper ion, a zinc ion, a zirconium ion, a germanium ion, a boron ion, a titanium ion or a silicon ion, and more preferably a sodium ion.

In fact, the above structure of the compound of formula (VI) is a simplified structure, and the structure of the compound of formula (VI) can also be

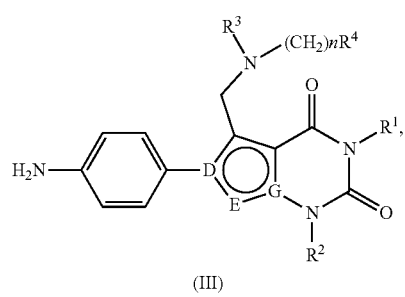

(III)

wherein, n, D, E, G R$^1$, R$^2$, R$^3$, and R$^4$ are as defined in formula (I);

the compound of formula (VI) is a mono-metal alkoxide or a bi-metal alkoxide, and M is selected from the group consisting of a monovalent metal cation, a divalent metal cation, a trivalent metal cation and a tetravalent metal cation, preferably a sodium ion, a potassium ion, a lithium ion, a calcium ion, a magnesium ion, a barium ion, an aluminum ion, a copper ion, a zinc ion, a zirconium ion, a germanium ion, a boron ion, a titanium ion or a silicon ion, and more preferably a sodium ion; and X is a halogen, and preferably fluorine, chlorine or bromine.

In the above scheme, the method further comprises a step of reacting a compound of formula (VII) with a metal alkoxide to obtain a compound of formula (VI):

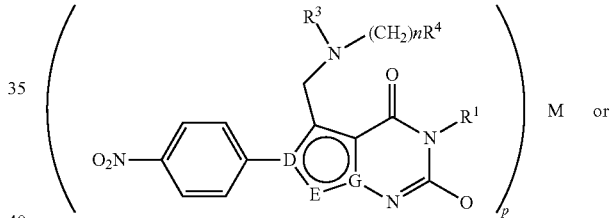

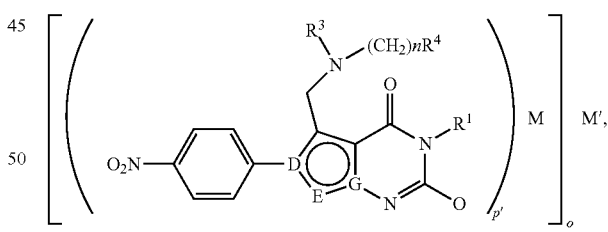

wherein, p is 1, 2, 3 or 4, p' is 4 or 9, o is 2, 3 or 4, and M and M' are different and are each selected from the group consisting of a monovalent metal cation, a divalent metal cation, a trivalent metal cation and a tetravalent metal cation, preferably a sodium ion, a potassium ion, a lithium ion, a calcium ion, a magnesium ion, a barium ion, an aluminum ion, a copper ion, a zinc ion, a zirconium ion, a germanium ion, a boron ion, a titanium ion or a silicon ion, and more preferably a sodium ion.

The present invention provides a method for preparing a compound of formula (I-1), characterized in that the method is as follows:

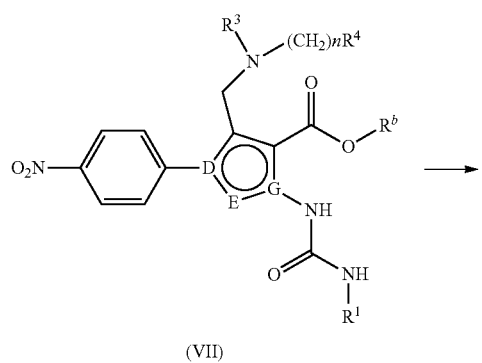

(VII)

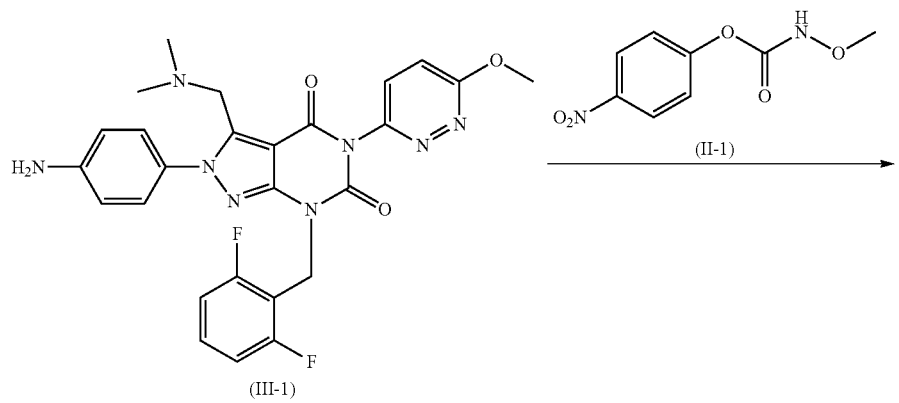

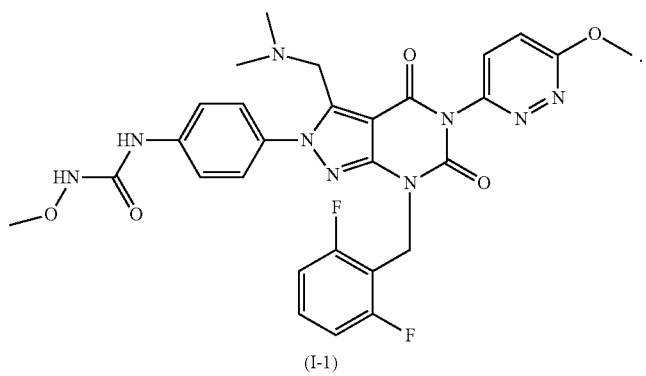

In the above scheme, the method also comprises the steps of:

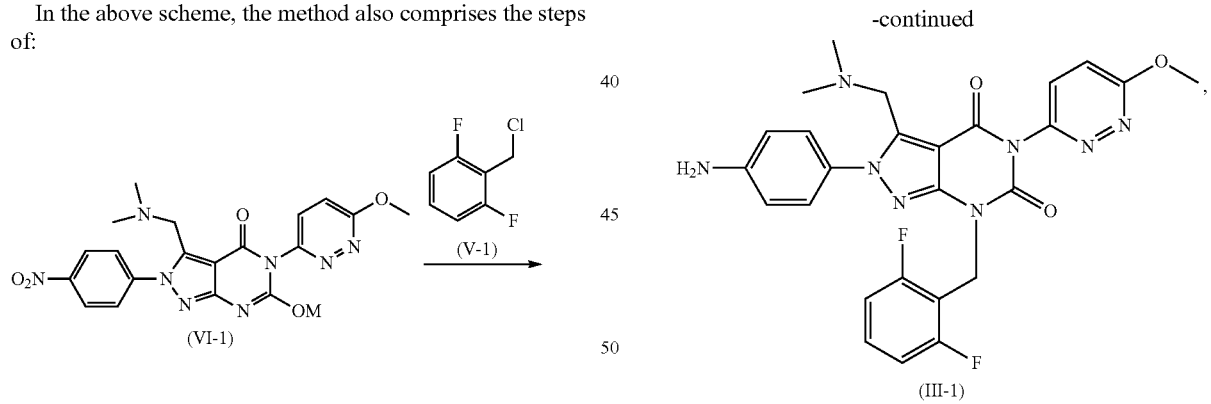

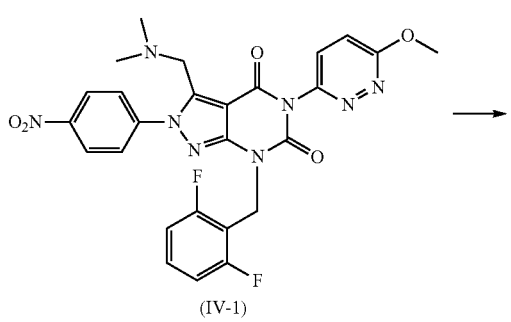

the compound of formula (VI-1) is a mono-metal alkoxide or a bi-metal alkoxide, and M is selected from the group consisting of a monovalent metal cation, a divalent metal cation, a trivalent metal cation and a tetravalent metal cation, preferably a sodium ion, a potassium ion, a lithium ion, a calcium ion, a magnesium ion, a barium ion, an aluminum ion, a copper ion, a zinc ion, a zirconium ion, a germanium ion, a boron ion, a titanium ion or a silicon ion, and more preferably a sodium ion.

In the above scheme, the method also comprises a step of reacting a compound of formula (VII-1) with a metal alkoxide to obtain a compound of formula (VI-1):

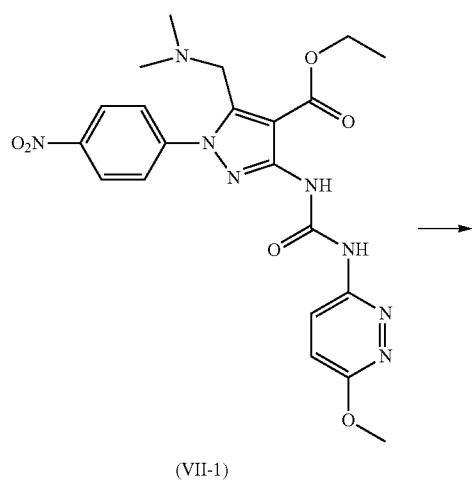

(VII-1)

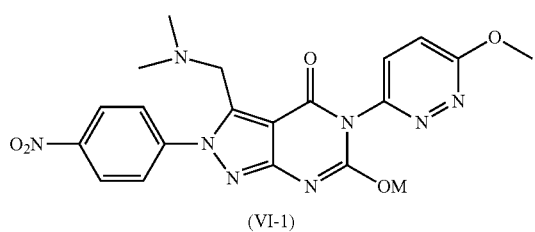

(VI-1)

Preferably, no acid is added in the post-treatment step of the method, and the acid is selected from the group consisting of an organic acid and an inorganic acid, the organic acid is preferably trifluoroacetic acid or acetic acid, and the inorganic acid is preferably hydrochloric acid.

The present invention also provides a compound of formula (VI):

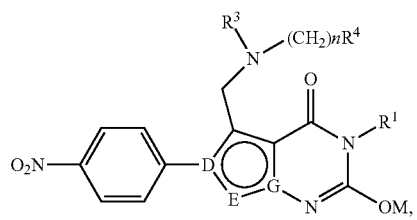

(VI)

or a salt thereof or a stereoisomer thereof, wherein, n, D, E, G R$^1$, R$^3$, and R$^4$ are as defined in formula (I);

the compound of formula (VI) is a mono-metal alkoxide or a bi-metal alkoxide, and M is selected from the group consisting of a monovalent metal cation, a divalent metal cation, a trivalent metal cation and a tetravalent metal cation, preferably a sodium ion, a potassium ion, a lithium ion, a calcium ion, a magnesium ion, a barium ion, an aluminum ion, a copper ion, a zinc ion, a zirconium ion, a germanium ion, a boron ion, a titanium ion or a silicon ion, and more preferably a sodium ion.

Preferably, the compound is

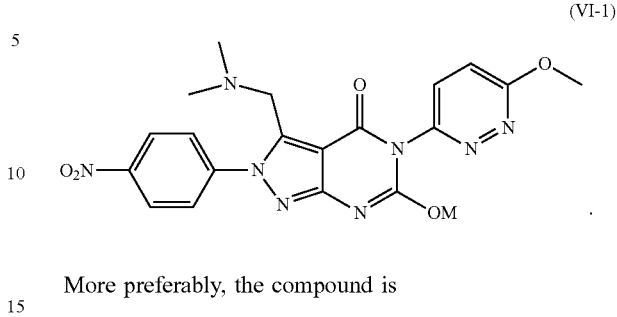

(VI-1)

More preferably, the compound is

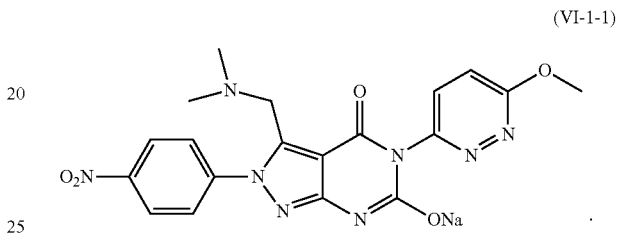

(VI-1-1)

The present invention provides a method for preparing a compound of formula (VI), characterized in that the method is a reaction of a compound of formula (VII) with a metal alkoxide to obtain the compound of formula (VI):

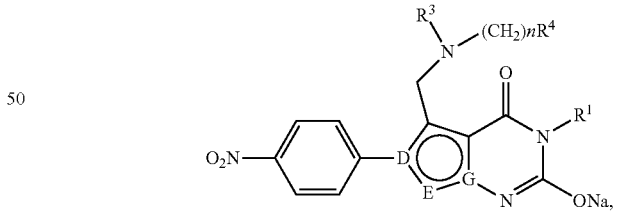

(VII)

(VI)

wherein, n, D, E, G, R$^1$, R$^3$, and R$^4$ are as defined in formula (I);

R$^b$ is alkyl;

the compound of formula (VI) is a mono-metal alkoxide or a bi-metal alkoxide, and M is selected from the group consisting of a monovalent metal cation, a divalent metal cation, a trivalent metal cation and a tetravalent metal cation, preferably a sodium ion, a potassium ion, a lithium ion, a calcium ion, a magnesium ion, a barium ion, an aluminum ion, a copper ion, a zinc ion, a zirconium ion, a germanium ion, a boron ion, a titanium ion or a silicon ion, and more preferably a sodium ion.

The present invention also provides a method for preparing a compound of formula (VI-1), characterized in that the method is a reaction of a compound of formula (VII-1) with a metal alkoxide to obtain the compound of formula (VI-1):

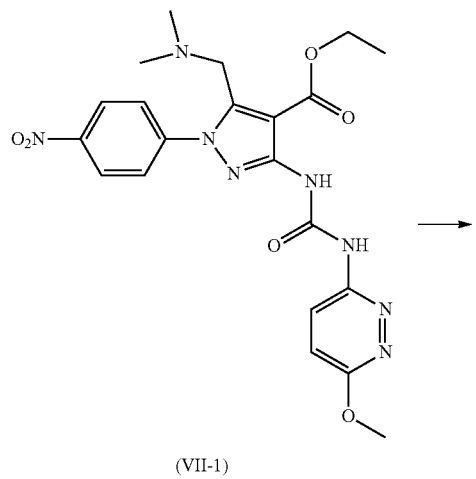

(VII-1)

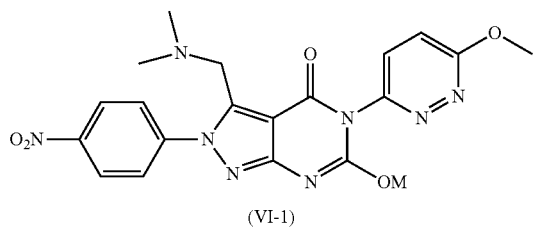

(VI-1)

wherein, the compound of formula (VI-1) is a mono-metal alkoxide or a bi-metal alkoxide, and M is selected from the group consisting of a monovalent metal cation, a divalent metal cation, a trivalent metal cation and a tetravalent metal cation, preferably a sodium ion, a potassium ion, a lithium ion, a calcium ion, a magnesium ion, a barium ion, an aluminum ion, a copper ion, a zinc ion, a zirconium ion, a germanium ion, a boron ion, a titanium ion or a silicon ion, and more preferably a sodium ion.

In the above scheme, no acid is added in the post-treatment step of the method, and the acid is selected from the group consisting of an organic acid and an inorganic acid, the organic acid is preferably trifluoroacetic acid or acetic acid, and the inorganic acid is preferably hydrochloric acid.

In fact, the above structure of the compound of formula (VI-1) is a simplified structure, and the structure of the compound of formula (VI) can also be

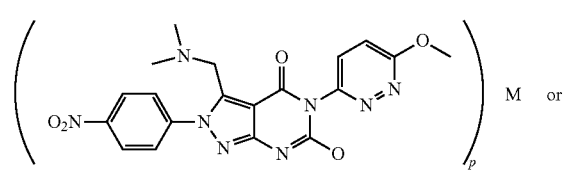 M or

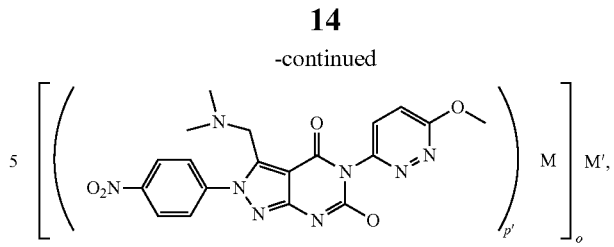

wherein, p is 1, 2, 3 or 4, p' is 4 or 9, o is 2, 3 or 4, and M and M' are different and are each selected from the group consisting of a monovalent metal cation, a divalent metal cation, a trivalent metal cation and a tetravalent metal cation, preferably a sodium ion, a potassium ion, a lithium ion, a calcium ion, a magnesium ion, a barium ion, an aluminum ion, a copper ion, a zinc ion, a zirconium ion, a germanium ion, a boron ion, a titanium ion or a silicon ion, and more preferably a sodium ion.

Preferably, the method is as follows:

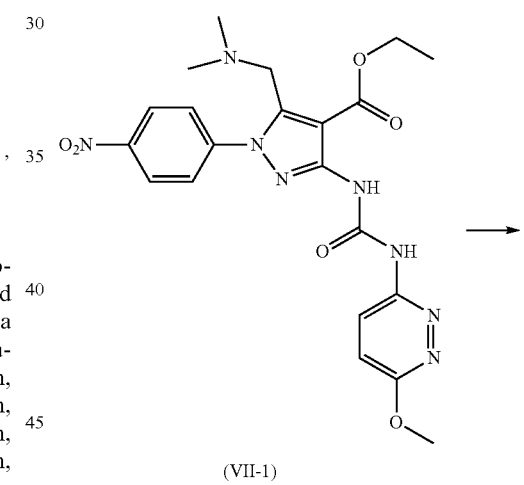

(VII-1)

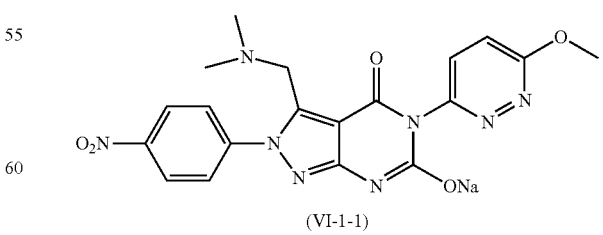

(VI-1-1)

The present invention also provides a method for preparing a compound of formula (I-1), characterized in that the method is as follows:

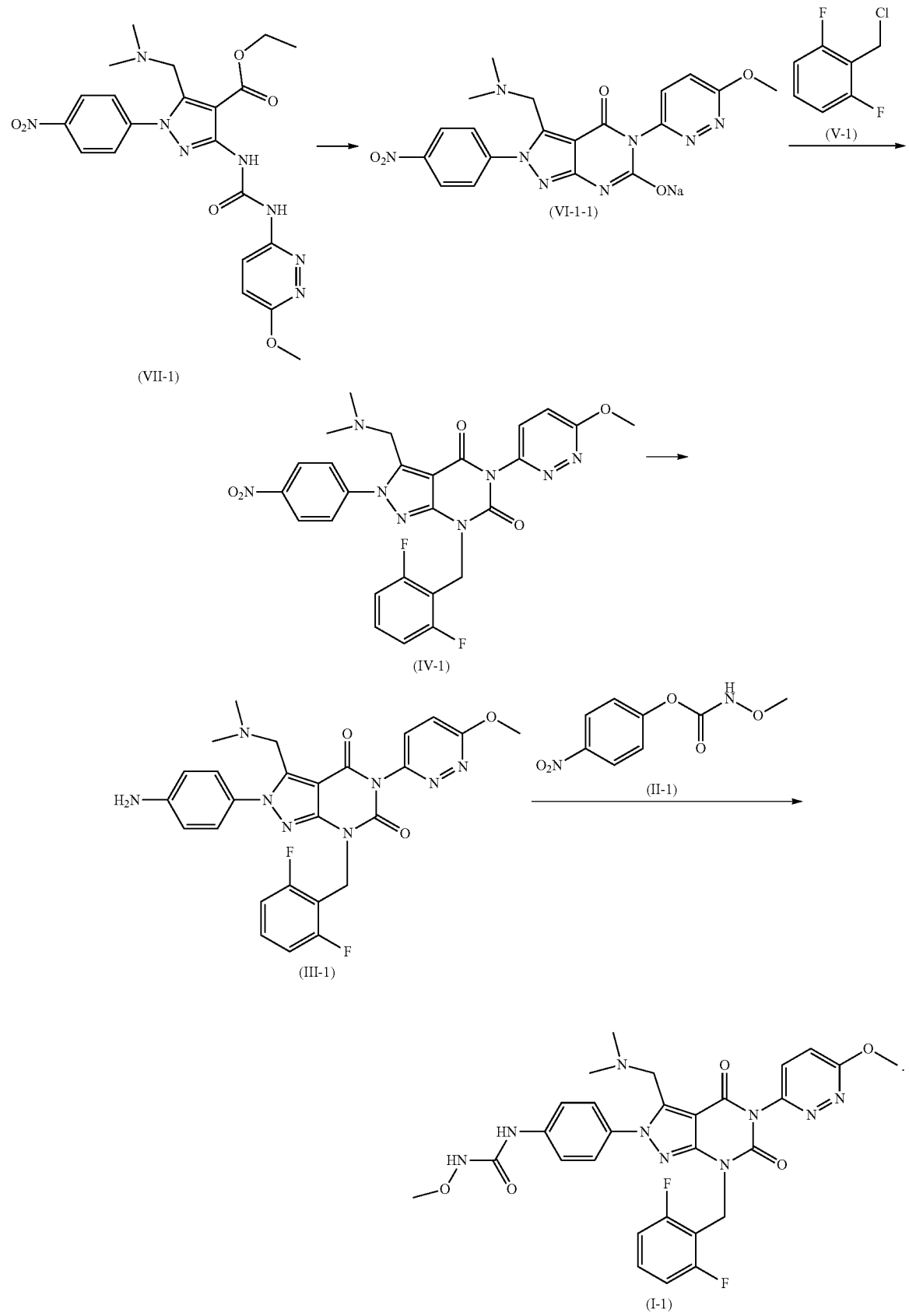

In the above scheme, no acid is added in the post-treatment step of the method for preparing the compound of formula (VI-1-1) from the compound of formula (VII-1), and the acid is selected from the group consisting of an organic acid and an inorganic acid, the organic acid is preferably trifluoroacetic acid or acetic acid, and the inorganic acid is preferably hydrochloric acid.

The present invention also provides a method for preparing a compound of formula (I-2), characterized in that the method is as follows:

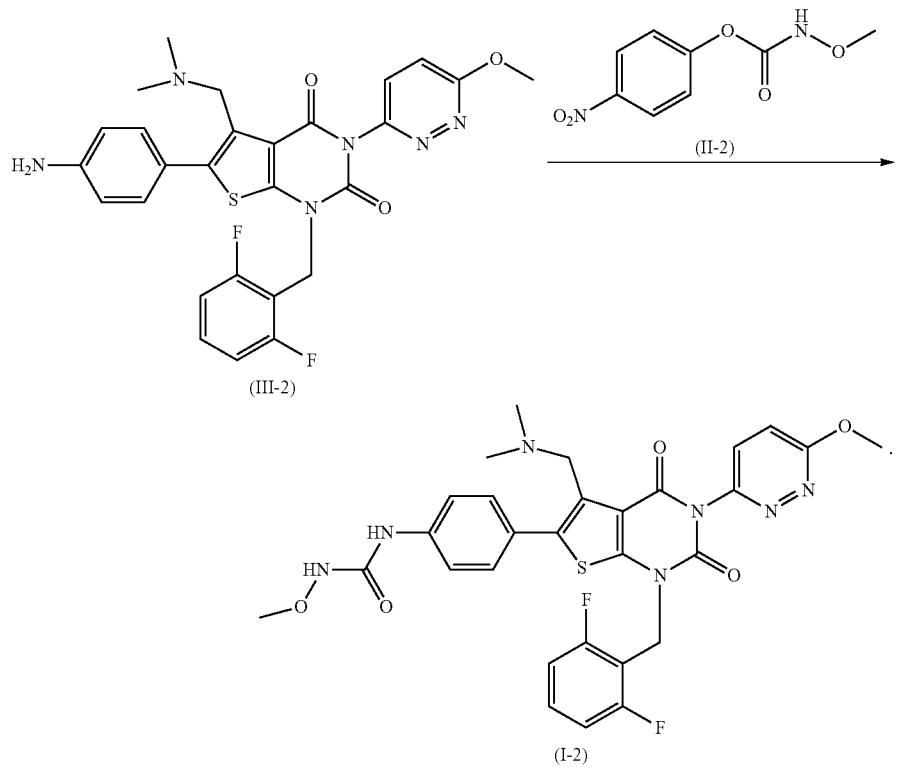

In the above scheme, the method also comprises the steps of:

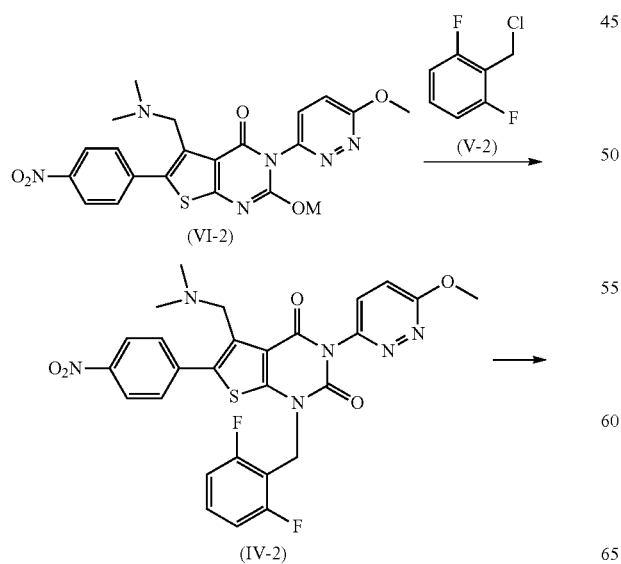

-continued

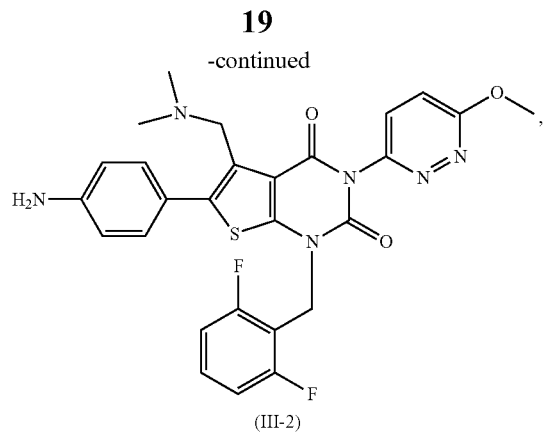

(III-2)

wherein the compound of formula (VI-2) is a mono-metal alkoxide or a bi-metal alkoxide, and M is selected from the group consisting of a monovalent metal cation, a divalent metal cation, a trivalent metal cation and a tetravalent metal cation, preferably a sodium ion, a potassium ion, a lithium ion, a calcium ion, a magnesium ion, a barium ion, an aluminum ion, a copper ion, a zinc ion, a zirconium ion, a germanium ion, a boron ion, a titanium ion or a silicon ion, and more preferably a sodium ion.

In the above scheme, the method also comprises a step of:

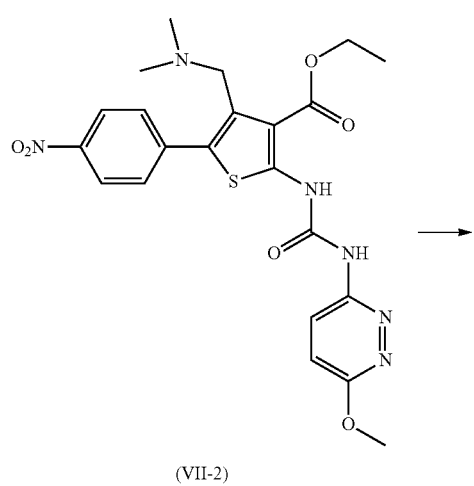

(VII-2)

-continued

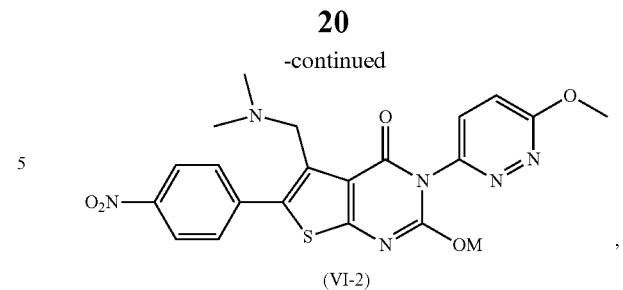

(VI-2)

Preferably, no acid is added in the post-treatment step of the method, and the acid is selected from the group consisting of an organic acid and an inorganic acid, the organic acid is preferably trifluoroacetic acid or acetic acid, and the inorganic acid is preferably hydrochloric acid.

In fact, the above structure of the compound of formula (VI-2) is a simplified structure, and the structure of the compound of formula (VI) can also be

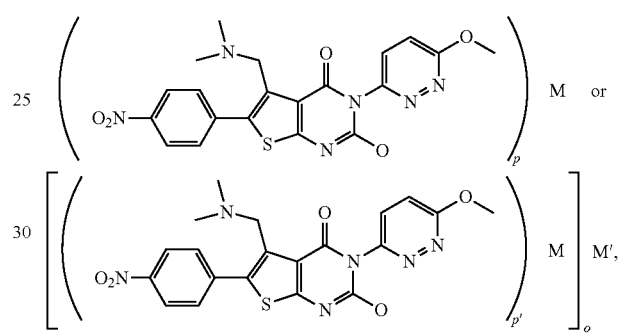

wherein, p is 1, 2, 3 or 4, p' is 4 or 9, o is 2, 3 or 4, and M and M' are different and are each selected from the group consisting of a monovalent metal cation, a divalent metal cation, a trivalent metal cation and a tetravalent metal cation, preferably a sodium ion, a potassium ion, a lithium ion, a calcium ion, a magnesium ion, a barium ion, an aluminum ion, a copper ion, a zinc ion, a zirconium ion, a germanium ion, a boron ion, a titanium ion or a silicon ion, and more preferably a sodium ion.

The present invention also provides a method for preparing a compound of formula (I-2), characterized in that the method is as follows:

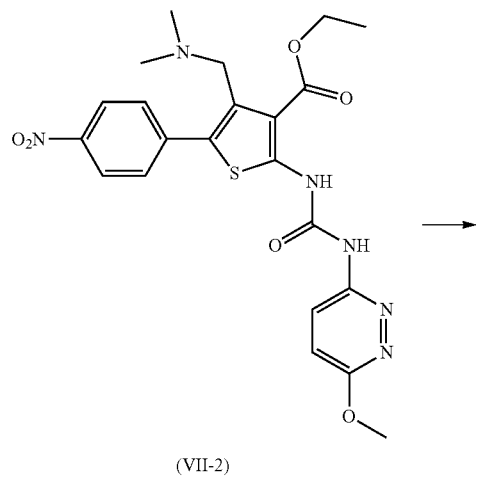

(VII-2)

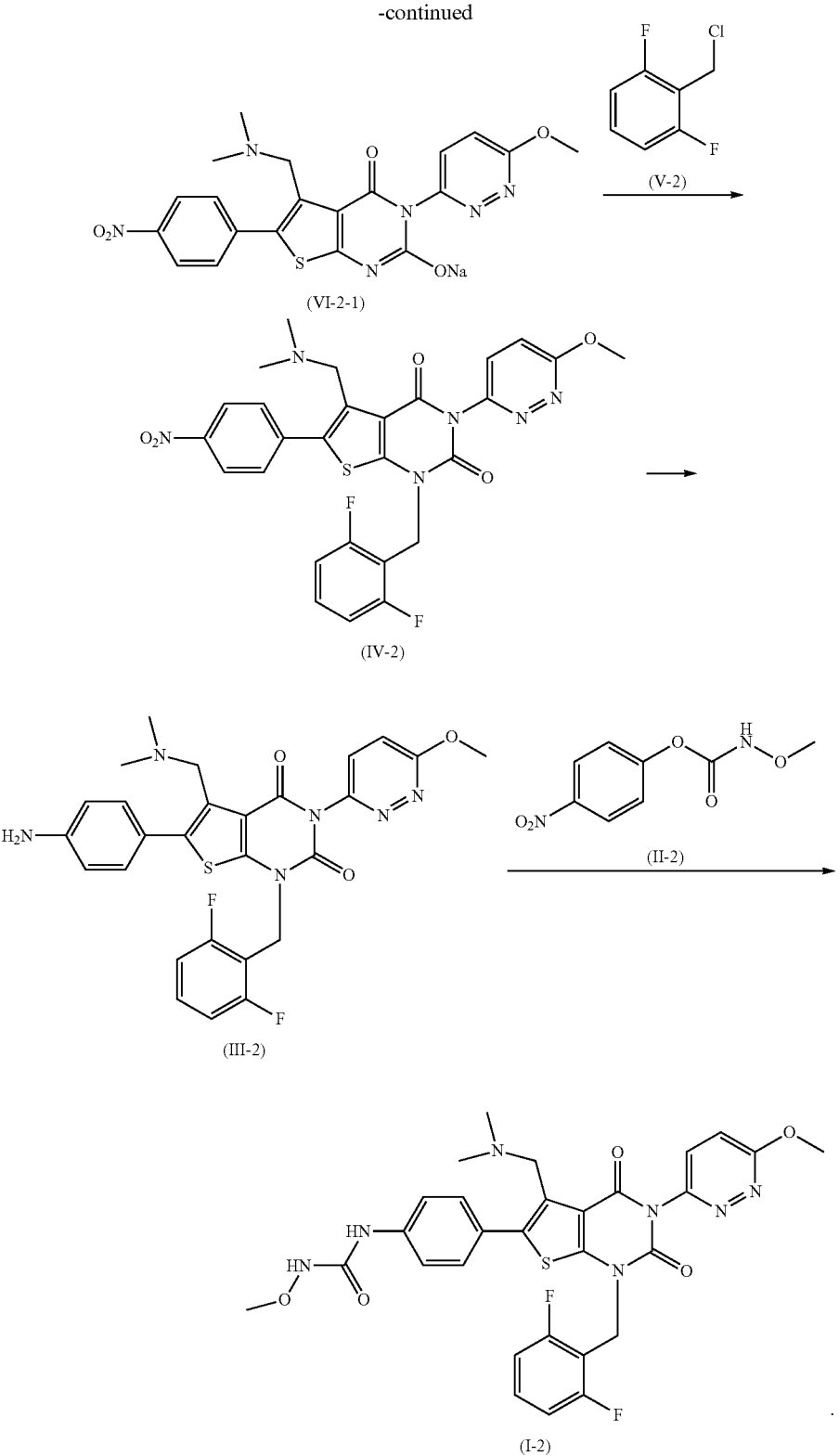

In the above scheme, no acid is added in the post-treatment step of the method for preparing the compound of formula (VI-2-1) from the compound of formula (VII-2), and the acid is selected from the group consisting of an organic acid and an inorganic acid, the organic acid is preferably trifluoroacetic acid or acetic acid, and the inorganic acid is preferably hydrochloric acid.

The present invention also provides a method for preparing a compound of formula (I-3), characterized in that the method is as follows:

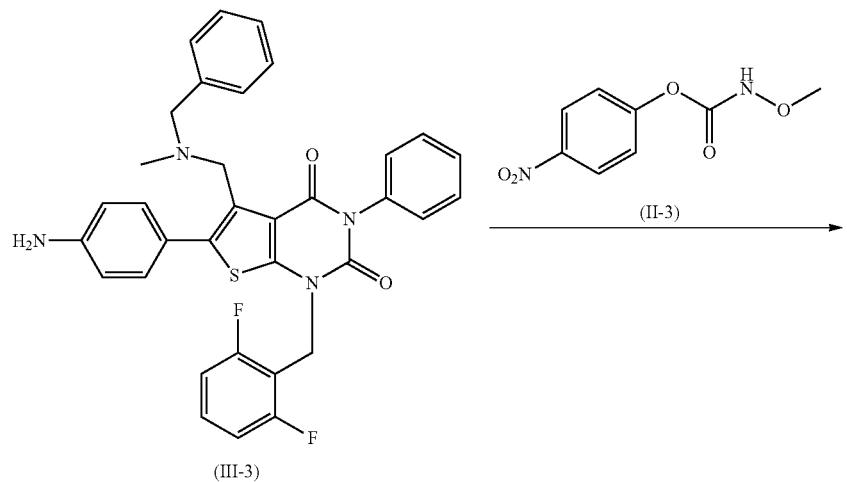
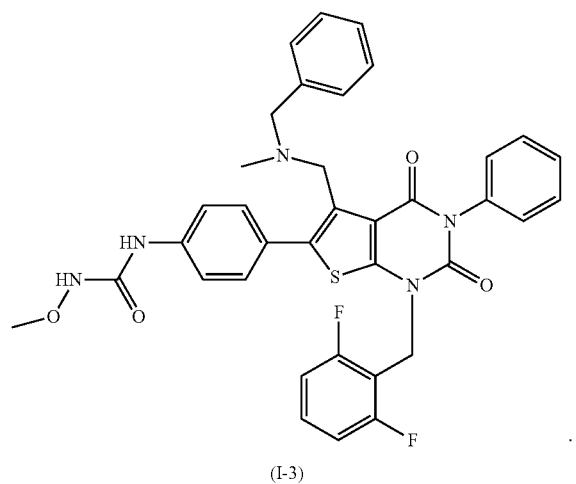
In the above scheme, the method also comprises the steps of:
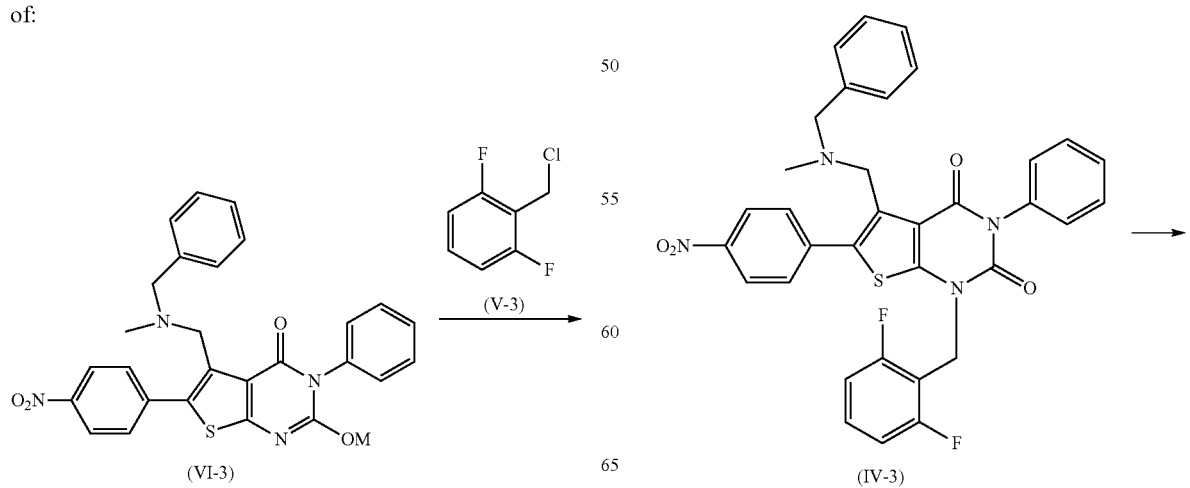

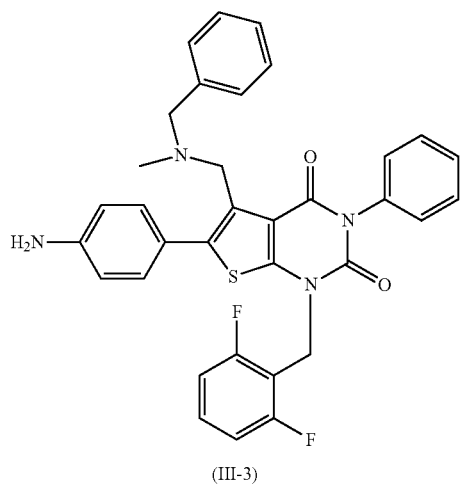

(III-3)

wherein the compound of formula (VI-3) is a mono-metal alkoxide or a bi-metal alkoxide, and M is selected from the group consisting of a monovalent metal cation, a divalent metal cation, a trivalent metal cation and a tetravalent metal cation, preferably a sodium ion, a potassium ion, a lithium ion, a calcium ion, a magnesium ion, a barium ion, an aluminum ion, a copper ion, a zinc ion, a zirconium ion, a germanium ion, a boron ion, a titanium ion or a silicon ion, and more preferably a sodium ion.

In the above scheme, the method also comprises a step of:

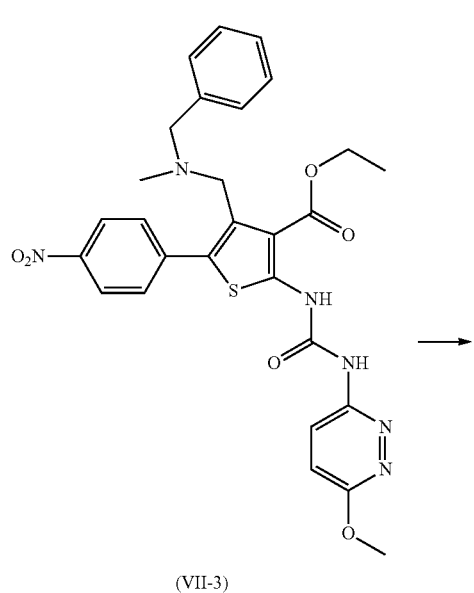

(VII-3)

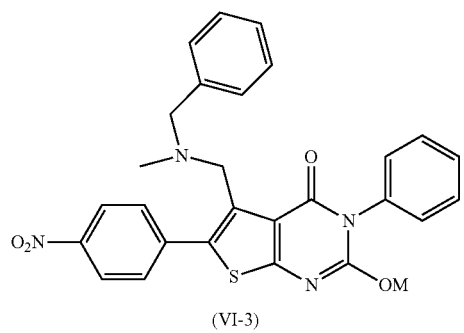

(VI-3)

Preferably, no acid is added in the post-treatment step of the method, and the acid is selected from the group consisting of an organic acid and an inorganic acid, the organic acid is preferably trifluoroacetic acid or acetic acid, and the inorganic acid is preferably hydrochloric acid.

In fact, the above structure of the compound of formula (VI-3) is a simplified structure, and the structure of the compound of formula (VI) can also be

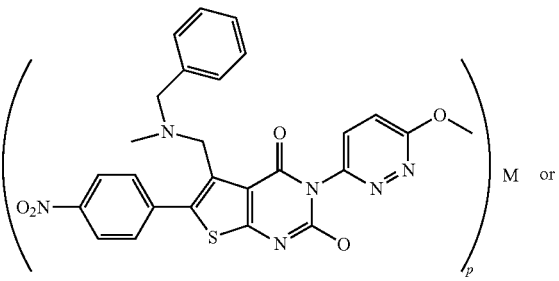

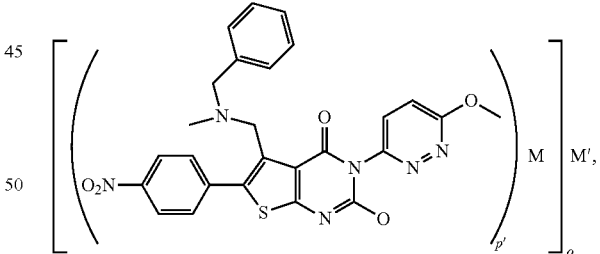

wherein, p is 1, 2, 3 or 4, p' is 4 or 9, o is 2, 3 or 4, and M and M' are different and are each selected from the group consisting of a monovalent metal cation, a divalent metal cation, a trivalent metal cation and a tetravalent metal cation, preferably a sodium ion, a potassium ion, a lithium ion, a calcium ion, a magnesium ion, a barium ion, an aluminum ion, a copper ion, a zinc ion, a zirconium ion, a germanium ion, a boron ion, a titanium ion or a silicon ion, and more preferably a sodium ion.

The present invention also provides a method for preparing a compound of formula (I-3), characterized in that the method is as follows:

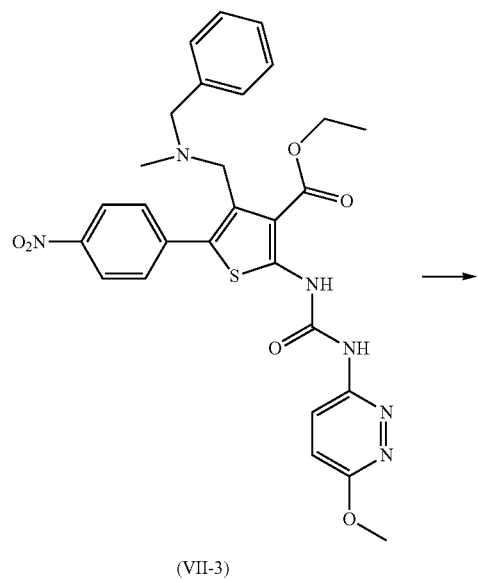
(VII-3)
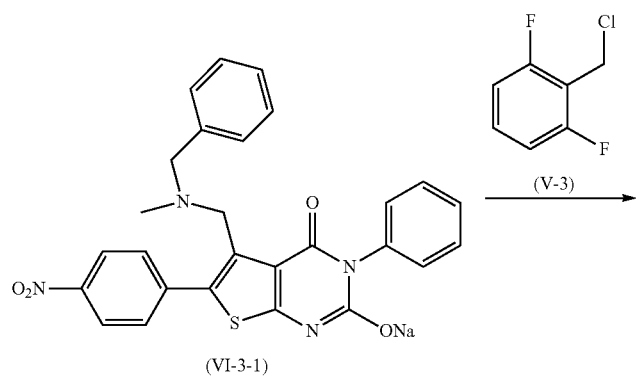
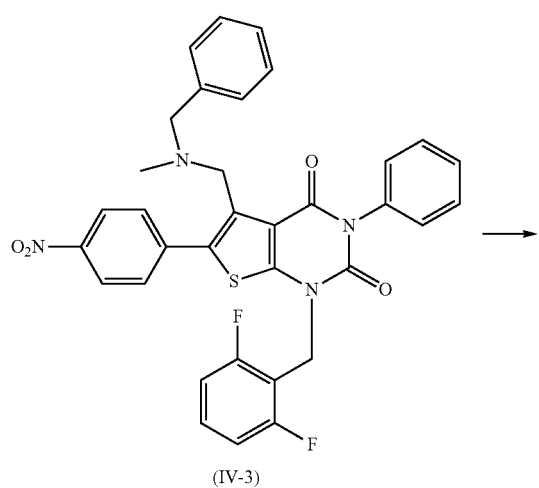
(IV-3)

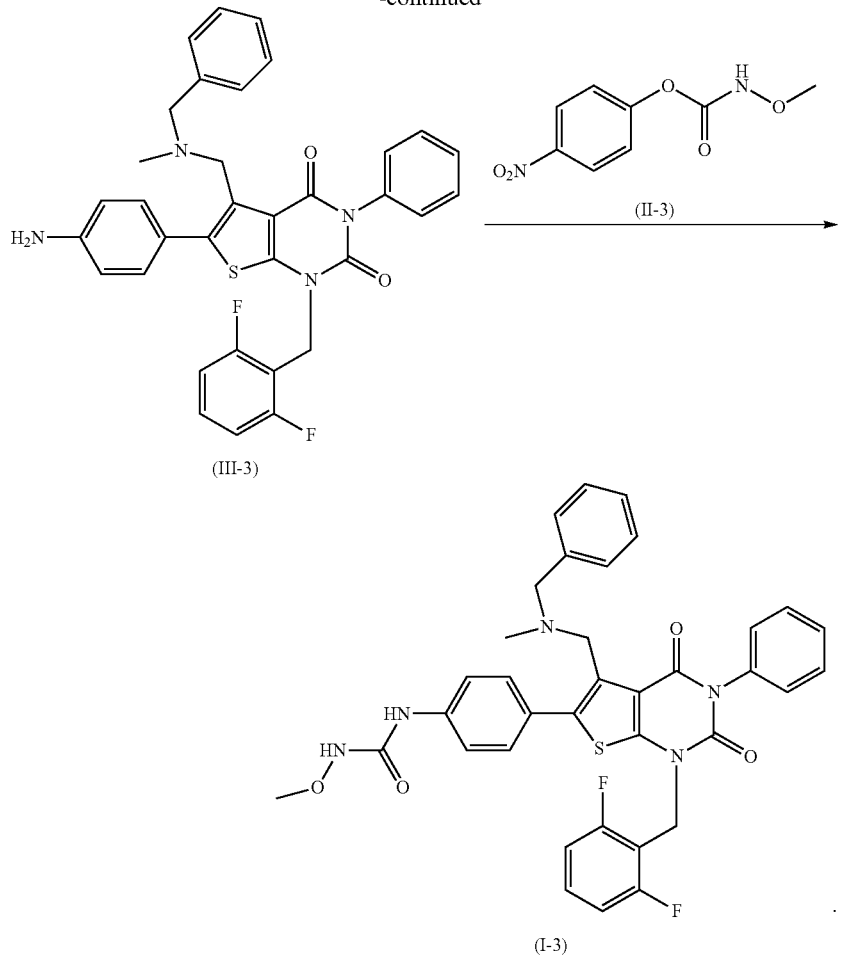

In the above scheme, no acid is added in the post-treatment step of the method for preparing the compound of formula (VI-3-1) from the compound of formula (VII-3), and the acid is selected from the group consisting of an organic acid and an inorganic acid, the organic acid is preferably trifluoroacetic acid or acetic acid, and the inorganic acid is preferably hydrochloric acid.

A method is provided for preparing a pharmaceutically acceptable salt of a compound of formula (I-1), formula (I-2) or formula (I-3), comprising the step(s) in the above schemes, and a step of reacting the compound of formula (I-1), formula (I-2) or formula (I-3) with an acid to obtain the pharmaceutically acceptable salt thereof, wherein the acid is selected from the group consisting of an organic acid and an inorganic acid, and preferably an organic acid; the organic acid is selected from the group consisting of acetic acid, maleic acid, fumaric acid, methanesulfonic acid, benzenesulfonic acid and p-toluenesulfonic acid, and preferably acetic acid; and the inorganic acid is selected from the group consisting of hydrochloric acid, hydrobromic acid, sulfuric acid and phosphoric acid.

DETAILED DESCRIPTION OF THE INVENTION

In order to understand the present invention more easily, certain technical and scientific terms are specifically defined below. Unless otherwise definitely and obviously defined in this document, all other technical and scientific terms used herein have the meaning commonly understood by one of ordinary skill in the art to which the present invention belongs.

The term "halogen" or "halogen atom" used in the present invention refers to fluorine, chlorine, bromine or iodine.

The term "alkyl" used in the present invention refers to a linear or branched alkyl having 1 to 20 carbon atoms, including for example "$C_{1-6}$ alkyl", "$C_{1-4}$ alkyl" and the like. The specific examples of alkyl include, but are not limited to: methyl, ethyl, n-propyl, isopropyl, n-butyl, isobutyl, sec-butyl, tert-butyl, n-pentyl, isopentyl, 2-methylbutyl, neo-pentyl, 1-ethylpropyl, n-hexyl, isohexyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, 1,2-dimethylpropyl and the like.

The term "alkenyl" used in the present invention refers to a linear or branched group having 2 to 20 carbon atoms and at least one carbon-carbon double bond, including for example "$C_{2-6}$ alkenyl", "$C_{2-4}$ alkenyl" and the like. The examples of alkenyl include, but are not limited to: vinyl, propenyl, 2-butenyl, 2-pentenyl, 3-pentenyl, 2-hexenyl, 3-hexenyl, and the like.

The term "alkynyl" used in the present invention refers to a linear or branched group having 2 to 20 carbon atoms and at least one carbon-carbon triple bond, including for example "$C_{2-6}$ alkynyl", "$C_{2-4}$ alkynyl" and the like. The examples of alkynyl include, but are not limited to: ethynyl, propynyl, 2-butynyl, 2-pentynyl, 3-pentynyl, 4-methyl-2-pentynyl, 2-hexynyl, 3-hexynyl, 5-methyl-2-hexynyl and the like.

The term "haloalkyl" used in the present invention refers to a group derived from an "alkyl" in which one or more hydrogen atoms are substituted by one or more "halogen atoms", and the terms "halogen atom" and "alkyl" are as defined above.

The term "hydroxy alkyl or hydroxyalkyl" used in the present invention refers to a group derived from an "alkyl" in which one or more hydrogen atoms are substituted by one or more "hydroxy", and the term "alkyl" is as defined above.

The term "alkoxy, haloalkoxy, alkylcarbonyl, alkoxycarbonyl, alkoxycarbonyl, carbonylalkoxy, alkylcarbonylamino, alkylaminocarbonyl, alkylamino, dialkylamino, alkylsulfonylamino or alkylsulfonyl" used in the present invention refers to a group with a linkage form of alkyl-O—, haloalkyl-O—, alkyl-C(O)—, alkyl-O—C(O)—, C(O)-alkyl-O—, alkyl-C(O)—NH—, alkyl-NH—C(O)—, alkyl-NH—, (alkyl)$_2$-N—, alkyl-S(O)$_2$—NH— or alkyl-S(O)$_2$—, wherein the terms "alkyl, haloalkyl" are as defined above.

The term "oxo" used in the present invention refers to an =O group.

The term "cycloalkyl" used in the present invention refers to a saturated or partially unsaturated monocyclic or polycyclic hydrocarbon group having 3 to 20 carbon atoms, preferably 3 to 12 carbon atoms, more preferably 3 to 10 carbon atoms, and most preferably 3 to 6 carbon atoms. Non-limiting examples of monocyclic cycloalkyl include cyclopropyl, cyclobutyl, cyclopentyl, cyclopentenyl, cyclohexyl, cyclohexenyl, cyclohexadienyl, cycloheptyl, cycloheptatrienyl, cyclooctyl and the like, and preferably cyclopropyl or cyclohexenyl. Polycyclic cycloalkyl includes a cycloalkyl having a spiro ring, fused ring or bridged ring.

The term "aryl" used in the present invention refers to a 6 to 14 membered all-carbon monocyclic ring or polycyclic fused ring (i.e. each ring in the system shares an adjacent pair of carbon atoms with another ring in the system) having a conjugated π-electron system, preferably 6 to 10 membered aryl, more preferably phenyl and naphthyl, and most preferably phenyl.

The term "heterocyclyl" used in the present invention refers to a 3 to 20 membered saturated or partially unsaturated monocyclic or polycyclic hydrocarbon group, wherein one or more ring atoms are heteroatoms (for example nitrogen atoms, oxygen atoms or sulfur atoms), with the remaining ring atoms being carbon atoms. Optionally, the ring atoms (for example, carbon atoms, nitrogen atoms or sulfur atoms) of the cyclic structure can be oxidized. Preferably, the heterocyclyl has 3 to 12 or 5 to 12 ring atoms wherein 1 to 4 atoms are heteroatoms, more preferably 3 to 8 ring atoms, and more preferably 5 to 6 ring atoms. Non-limiting examples of monocyclic heterocyclyl include pyrrolidinyl, piperidinyl, piperazinyl, morpholinyl, thiomorpholinyl, homopiperazinyl, pyranyl, tetrahydrofuranyl and the like. Polycyclic heterocyclyl includes a heterocyclyl having a spiro ring, fused ring or bridged ring.

The term "heteroaryl" used in the present invention refers to a 5 to 14-membered aryl having 1 to 4 heteroatoms including O, S and N as ring atoms and the remaining ring atoms being carbon atoms. The heteroaryl is preferably a 5 to 10 membered heteroaryl, and more preferably a 5 or 6 membered heteroaryl. The specific examples of heteroaryl include, but are not limited to furyl, thienyl, pyrrolyl, thiazolyl, isothiazolyl, thiadiazolyl, oxazolyl, isoxazolyl, oxadiazolyl, imidazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, pyridyl, 2-pyridonyl, 4-pyridonyl, pyrimidyl, pyridazinyl, pyrazinyl, 1,2,3-triazinyl, 1,3,5-triazinyl, 1,2,4,5-tetrazinyl, azacycloheptatrienyl, 1,3-diazacycloheptatrienyl, azacyclooctatetraenyl and the like. The heteroaryl can also be fused to the ring of aryl, heterocyclyl or cycloalkyl.

The expression "carbon atoms, nitrogen atoms or sulfur atoms are oxidized" used in the present invention refers to the formation of a C=O, N=O, S=O or SO$_2$ structure.

The term "alcohol solvent" used in the present invention refers to a group derived from a "$C_{1-6}$ alkyl" in which one or more hydrogen atoms are substituted by one or more "hydroxys", and the terms "hydroxy" and "$C_{1-6}$ alkyl" are as defined above. Its specific examples include, but are not limited to: methanol, ethanol, isopropanol, n-propanol, isopentanol and trifluoroethanol.

The term "metal alkoxide" used in the present invention refers to a compound formed by the substitution of a hydrogen of a hydroxy in an alcohol by a metal element, and is also called a metal acid ester or a metal alkoxy compound. Metal alkoxide can be divided into mono-metal alkoxide, bi-metal alkoxide and the like, and the metal element can be a monovalent, divalent, trivalent or tetravalent metal. The specific examples of metal alkoxide include, but are not limited to: lithium methoxide, sodium methoxide, sodium ethoxide, calcium dimethoxide, aluminum tripropoxide, silicon tetraethoxide, magnesium aluminum ethoxide, magnesium aluminum n-butoxide and the like.

The term "stereoisomerism" used in the present invention can be classified into conformational isomerism and configurational isomerism, while the configurational isomerism can be further classified into cis-trans isomerism and optical isomerism (or enantiomerism). Conformational isomerism refers to a stereoisomerism in which an organic molecule with a certain configuration causes different spatial arrangement modes of atoms or radicals of the molecule due to the rotation or distortion of carbon-carbon single bonds, common examples include structures of alkanes and cycloalkanes, such as chair conformation and boat conformation of cyclohexane. "Optical isomers (or enantiomers)" refer to that when the compound of the present invention contains one or more asymmetric centers, it can be used as a racemate and a racemate mixture, a single enantiomer, a mixture of diastereomers and a single diastereomer. The compound of the present invention has asymmetric centers, each of which can independently generate two optical isomers. The scope of the present invention covers all possible optical isomers and mixtures of diastereomers and pure or partially pure compounds. If the compound of the present invention has an olefinic double bond, unless otherwise indicated, the present invention covers a cis-isomer and a trans-isomer. The compound of the present invention can exist in its tautomer forms, in which one or more double bonds shift thereby having different hydrogen attachment points. For example, a ketone and its enol form are keto-enol tautomers. The present invention encompasses all tautomers and mixtures thereof. All enantiomers, diastereomers, racemes, mesomers, cis-trans isomers, tautomers, geometric isomers, epimers and mixtures thereof are included in the scope of the present invention.

Advantageous Effects of the Present Invention

Compared with the prior art, the technical solution for preparing the compound of formula (I) of the present invention has the following advantages:

(1) The starting materials and intermediates of the present invention are different from the prior art, the present invention has provided a synthesis method with a completely different approach, and the starting materials and reactants are simple and easy to purchase.

(2) The yield is increased, the yield of the final product disclosed in the prior art is 24.7%, while the yield of the final product of the present invention is 80%.

(3) The post-treatment is simple, after the reaction is completed, a solid can be obtained directly by filtration, there is no need for column chromatography purification, and the acid treatment is avoided, therefore, the post-treatment method is conducive to industrial production.

Preferred Embodiments

The present invention will be further described with reference to the following examples, which should not be considered as limiting the scope of the present invention.

In the examples of the present invention, the experiment methods that do not specify the specific conditions are generally conducted in accordance with conventional conditions, or in accordance with conditions recommended by the material or product manufacturers. The reagents without a specific source are commercially available conventional reagents.

EXAMPLES

The structures of the compounds were identified by nuclear magnetic resonance (NMR) and/or mass spectrometry (MS). NMR shifts (δ) were given in $10^{-6}$ (ppm). NMR was determined by a Bruker AVANCE-500 machine. The solvents for determination were deuterated reagents, and the internal standard was tetramethylsilane (TMS).

Ethyl 5-((dimethyl amino)methyl)-3-(3-(6-methoxypyridazin-3-yl)ureido)-1-(4-nitrophenyl)-1H-pyrazole-4-carboxylate (the compound of formula (VII-1)) can be prepared by referring to the method disclosed in Example 9 of the patent application WO2015062391A1 (publication date: 7 May 2015),

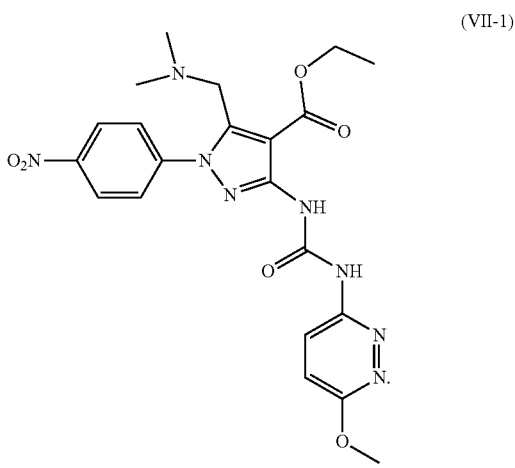 [SMILES: CCOC(=O)c1c(NC(=O)Nc2ccc(OC)nn2)nn(-c2ccc([N+](=O)[O-])cc2)c1CN(C)C]

Example 1. Preparation of 1-(4-(7-(2,6-difluorobenzyl)-3-((dimethylamino)methyl)-5-(6-methoxypyridazin-3-yl)-4,6-dioxo-4,5,6,7-tetrahydro-2H-pyrazolo[3,4-d]pyrimidin-2-yl)phenyl)-3-methoxyurea

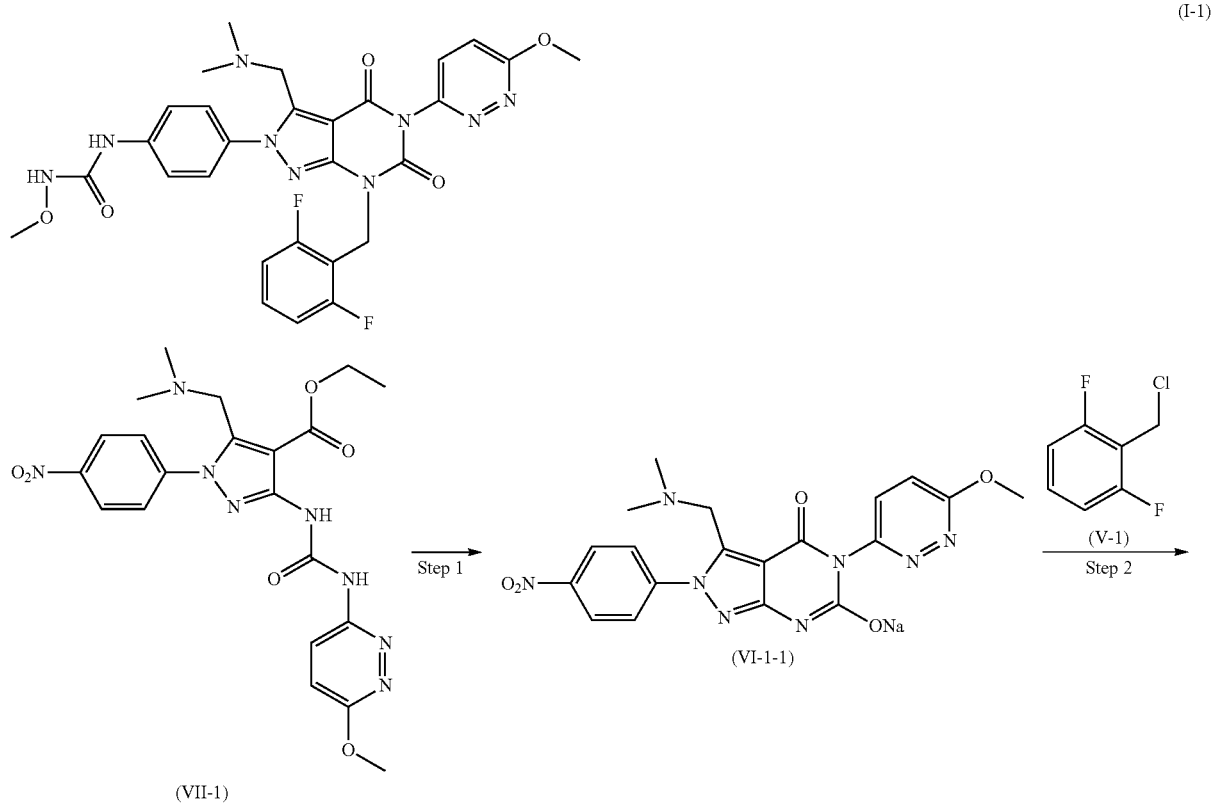

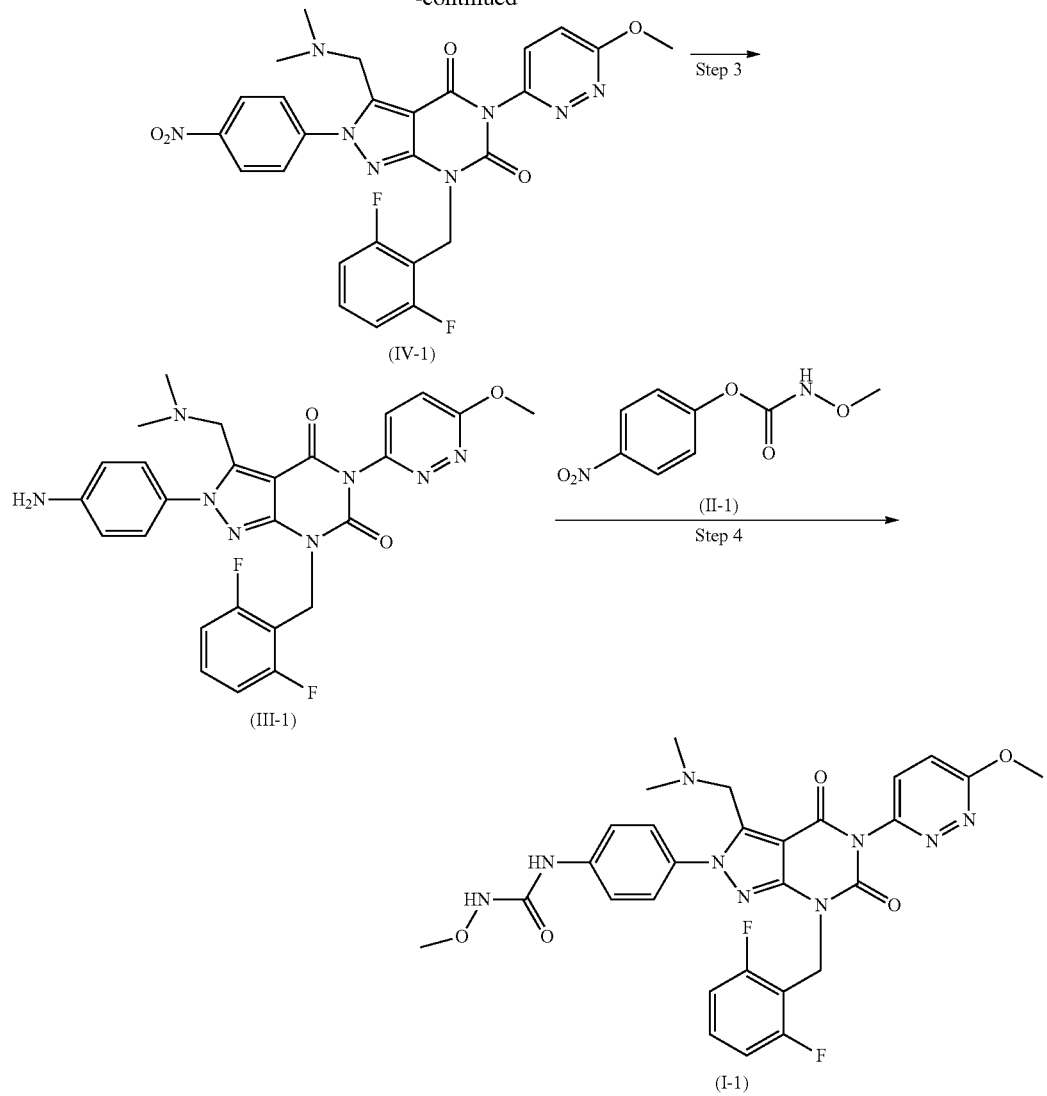

Step 1. Preparation of the Compound of Formula (VI-1-1)

The starting compound VII-1 (90 g) was suspended in methanol (900 mL), then a 30% solution (101 g) of sodium methoxide in methanol was added. The reaction solution was stirred in an oil bath at 30° C. for about 15 hours. After completion of the reaction, isopropanol (1.8 L) was added to the reaction solution, stirred well, cooled to room temperature, and then frozen for 4 hours to precipitate a crystal. The mixture was filtered to collect a filter cake, which was pulped in acetone (320 mL) for 1.5 hours. The mixture was cooled in an ice bath, and filtered to collect a filter cake. The filter cake was dried under vacuum to obtain the title product (65.9 g), yield: 81.0%, purity: 99.27%.

Step 2. Preparation of the Compound of Formula (IV-1)

The starting compound VI-1-1 (1100 g) and N,N-dimethylformamide (7.0 kg) were added to a reaction flask and stirred well, then 2,6-difluorochlorobenzyl (427.2 g) and N,N-diisopropylethylamine (926.4 g) were added. The reaction solution was warmed up to 80-110° C., and stirred for 1-3 hours. After completion of the reaction, the reaction solution was cooled. Purified water (30.0 kg) was added to another reaction flask, and cooled to 0-10° C. The reaction solution was poured into the pre-cooled purified water under stirring, stirred for 0.5 h and spin-filtrated. The filter cake was washed with purified water (25.0 kg×2) and collected.

A mixed solvent of acetone/purified water (5.2 kg of acetone/2.2 kg of purified water) and the above filter cake were added to a reaction flask, and heated to reflux under stirring for 0.5 h. The reaction solution was cooled to 0-10° C., stirred for 2 hours, and filtered. The filter cake was washed with a mixed solvent of acetone/purified water (1.2 kg of acetone/0.5 kg of purified water), and dried to obtain a solid (1203.1 g), yield: 95%, purity: 93.64%.

Step 3. Preparation of the Compound of Formula (III-1)

The starting compound IV-1 (1201.1 g) and anhydrous ethanol (4.0 kg) were added to a reaction flask. After cooling to 0-15° C. under stirring, the reaction solution was added with hydrochloric acid (5.8 kg) and stirred well. The reaction solution was added with stannous chloride dihydrate (2400.6 g), and stirred at 15-40° C. for 1-3.5 hours. After completion of the reaction, the pH of the reaction solution was adjusted to 11-12 with a 25% (w/w) sodium hydroxide solution (4.1 kg of sodium hydroxide in 12.3 kg of purified water) at a temperature below 25° C. The reaction solution was spin-filtrated, and the filter cake was washed with purified water (10.0 kg). The filter cake was dried, purified by column chromatography, and concentrated under reduced pressure. The residue was added with n-hexane (7.0 kg), stirred at room temperature for 0.5 h, filtered and dried to obtain a solid (972.6 g), yield: 90%, purity: 98.01%.

Step 4. Preparation of the Compound of Formula (I-1)

The starting compound III-1 (970.6 g), tetrahydrofuran (11.5 kg), 4-nitrophenyl methoxycarbamate (423.8 g, prepared according to the method disclosed in the patent application WO2011090935A1), N,N-diisopropylethylamine (704.1 g) were added to a reaction flask, and the reaction solution was stirred at 15-40° C. for 16-18 hours. After completion of the reaction, the reaction solution was cooled to 0-10° C., stirred for 2 hours and filtrated. The filter cake was added into tetrahydrofuran (6.0 kg), stirred at room temperature for 1.5 hours and filtered. The filter cake was washed with tetrahydrofuran (1.0 kg), and dried to obtain a solid (807.9 g), yield: 80%.

The above resulting crude product (805.9 g) and a mixed solvent of acetone/purified water (7897.8 g of acetone/2014.8 g of purified water) were added into a reaction flask. The reaction solution was heated to reflux, stirred until it became clear, and then filtered while it was still hot. The filtrate was naturally cooled to room temperature, and stirred for 20-24 hours. The mixture was cooled to 0-15° C., stirred for 2 hours and filtered. The filter cake was washed with purified water (2.5 kg×2), and dried to obtain a solid (606.1 g), yield: 90%, purity: 99.9%.

MS m/z (ESI): 608.3 [M+1].

$^1$H-NMR (400 MHz, DMSO-d$_6$) δ 9.69 (s, 1H), 9.17 (s, 1H), 7.79-7.82 (d, 2H), 7.73-7.75 (d, 1H), 7.68-7.70 (d, 2H), 7.42-7.45 (d, 1H), 7.37-7.41 (m, 1H), 7.06-7.12 (m, 2H), 5.28 (s, 2H), 4.09 (s, 3H), 3.67 (s, 2H), 3.66 (s, 3H), 2.17 (s, 6H).

Example 2. The Compound 1-(4-(1-(2,6-difluorobenzyl)-5-((dimethylamino)methyl)-3-(6-methoxypyridazin-3-yl)-2,4-dioxo-1,2,3,4-tetrahydrothieno[2,3-d]pyrimidin-6-yl)phenyl)-3-methoxyurea (Formula (I-2)) was Prepared by Referring to the Method in Example 1 Above

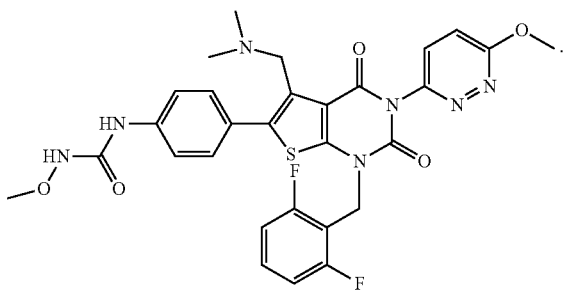

(I-2)

Example 3. The Compound 1-(4-(5-((benzyl (methyl)amino)methyl)-1-(2,6-difluorobenzyl)-2,4-dioxo-3-phenyl-1,2,3,4-tetrahydrothieno[2,3-d]pyrimidin-6-yl)phenyl)-3-methoxyurea (Formula (I-3)) was Prepared by Referring to the Method in Example 1 Above

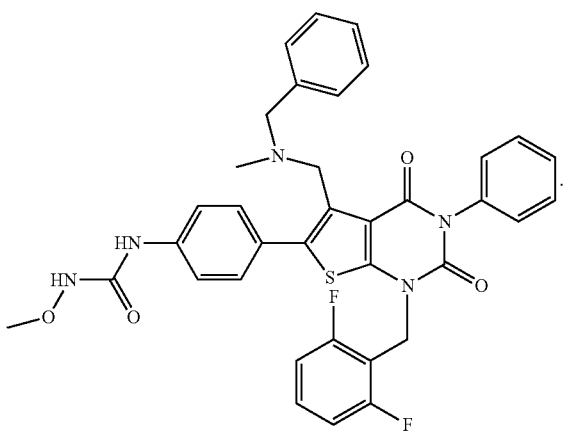

(I-3)

What is claimed is:
1. A method for preparing a compound of formula (I) or a stereoisomer thereof, wherein the method comprises reacting a compound of formula (III), a salt thereof or a stereoisomer thereof, with a compound of formula (II) or a salt thereof to obtain the compound of formula (I):

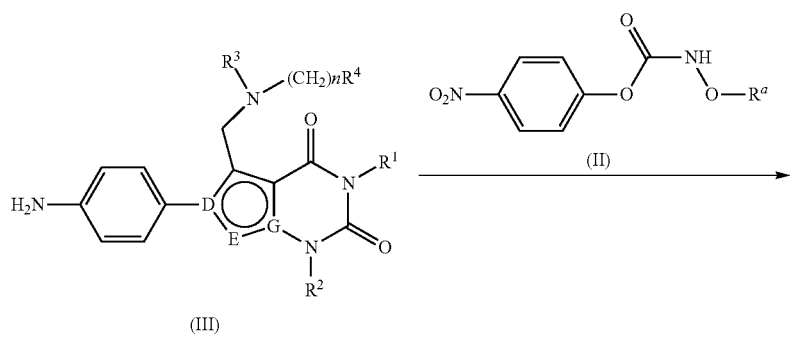

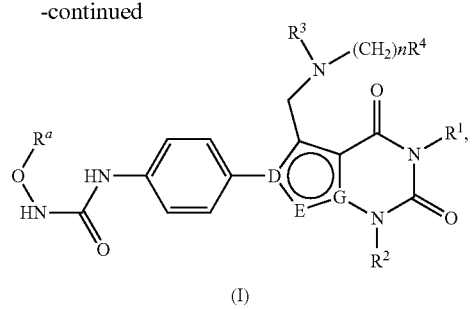

(I)

wherein:

G is C, D and E are N;

R[1] is selected from the group consisting of alkyl, cycloalkyl, heterocyclyl, aryl, heteroaryl and —OR[5], wherein the alkyl, cycloalkyl, heterocyclyl, aryl and heteroaryl are each independently and optionally further substituted by one or more substituents selected from the group consisting of halogen, cyano, nitro, alkyl, haloalkyl, hydroxyalkyl, alkenyl, alkynyl, cycloalkyl, heterocyclyl, aryl, heteroaryl, —OR[5], —C(O)OR[5], —OC(O)R[5], —NHS(O)$_m$R[5], —C(O)R[5], —NHC(O)R[5], —NHC(O)OR[5], —NR[6]R[7], —OC(O)NR[6]R[7], —C(O)NR[6]R[7], —NHC(O)NHR[5] and —NHC(O)NHOR[5];

R[2] is alkyl, wherein the alkyl is further substituted by one or more substituents selected from the group consisting of aryl and heteroaryl, wherein the aryl and heteroaryl are optionally further substituted by one or more substituents selected from the group consisting of halogen, alkyl, haloalkyl, cyano, nitro, —C(O)OR[5], —C(O)NR[6]R[7], —OC(O)NR[6]R[7], —OR[5], —NHS(O)$_m$R[5], —NHC(O)R[5] and —NR[6]R[7];

R[3] is alkyl;

R[4] is selected from the group consisting of hydrogen, cycloalkyl, heterocyclyl, aryl, heteroaryl, —OR[5], —NR[6]R[7] and —NR[6]S(O)$_m$R[5], wherein the cycloalkyl, heterocyclyl, aryl and heteroaryl are optionally further substituted by one or more substituents selected from the group consisting of halogen, oxo, alkyl, haloalkyl, hydroxyalkyl, —OR$_5$, —C(O)OR[5], —OC(O)R[5], —NR[7]S(O)$_m$R[5], —S(O)$_m$R[5], —C(O)R[5] and —NHC(O)R[5];

R[5] is selected from the group consisting of hydrogen, alkyl, cycloalkyl, heterocyclyl, aryl and heteroaryl, wherein the alkyl, cycloalkyl, heterocyclyl, aryl and heteroaryl are each independently and optionally further substituted by one or more substituents selected from the group consisting of alkyl, halogen, hydroxy, alkoxy, haloalkoxy, cycloalkyl, heterocyclyl, aryl, heteroaryl, carboxy and alkoxycarbonyl;

R[6] and R[7] are each independently selected from the group consisting of hydrogen, alkyl, cycloalkyl, heterocyclyl, aryl and heteroaryl, wherein the alkyl, cycloalkyl, heterocyclyl, aryl and heteroaryl are each independently and optionally further substituted by one or more substituents selected from the group consisting of alkyl, halogen, hydroxy, alkoxy, haloalkoxy, cycloalkyl, heterocyclyl, aryl, heteroaryl, carboxy and alkoxycarbonyl;

or, R[6] and R[7] together with the nitrogen atom to which they are attached form a heterocyclyl, wherein the heterocyclyl contains one or more heteroatoms selected from the group consisting of N, O and S(O)$_m$, and the heterocyclyl is optionally further substituted by one or more substituents selected from the group consisting of alkyl, halogen, hydroxy, alkoxy, haloalkoxy, cycloalkyl, heterocyclyl, aryl, heteroaryl, carboxy and alkoxycarbonyl;

R[a] is alkyl, wherein the alkyl is optionally further substituted by one or more substituents selected from the group consisting of alkyl, halogen, hydroxy, alkoxy, cycloalkyl, heterocyclyl, aryl, heteroaryl, carboxy and alkoxycarbonyl;

m is 0, 1 or 2; and n is 1, 2, 3 or 4.

2. The method according to claim 1, wherein the compound of formula (III), a salt thereof or a stereoisomer thereof, is prepared by the following method:

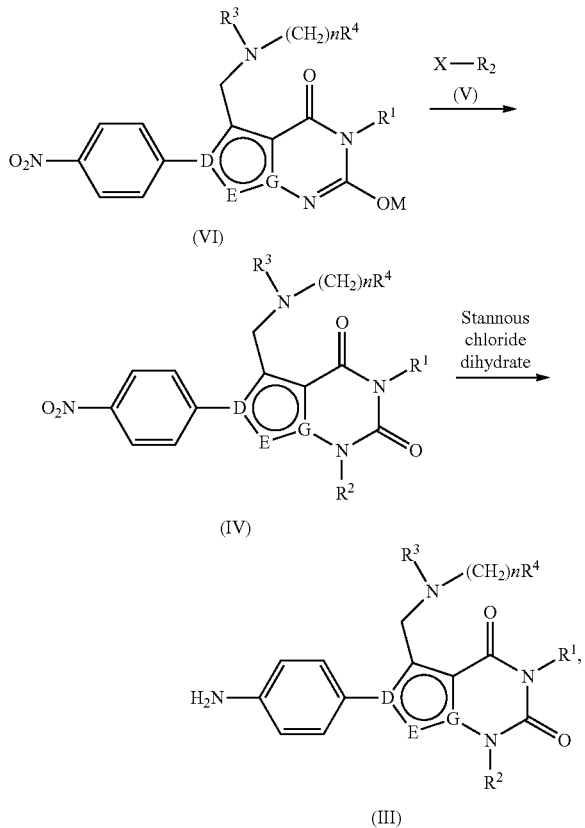

wherein:

X is halogen;

the compound of formula (VI) is a mono-metal alkoxide or a bi-metal alkoxide; and M is selected from the group consisting of a monovalent metal cation, a divalent metal cation, a trivalent metal cation and a tetravalent metal cation.

3. The method of claim 2, wherein the compound of formula (VI) is prepared by the following method:

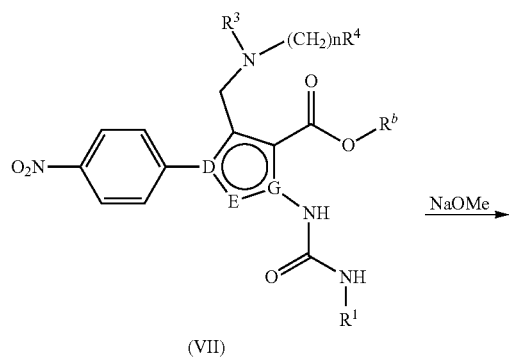

(VII)

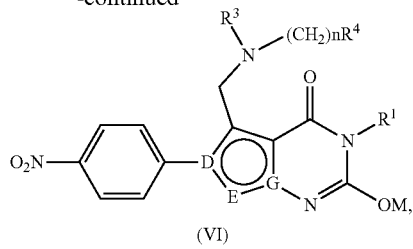

(VI)

wherein:

$R^b$ is alkyl.

4. The method according to claim 1, wherein the compound of formula (I) is a compound of formula (I-1) or a stereoisomer thereof, the compound of formula (II) is a compound of formula (II-1) or a salt thereof, and the compound of formula (III) is a compound of formula (III-1), a salt thereof or a stereoisomer thereof, wherein the method is as follows:

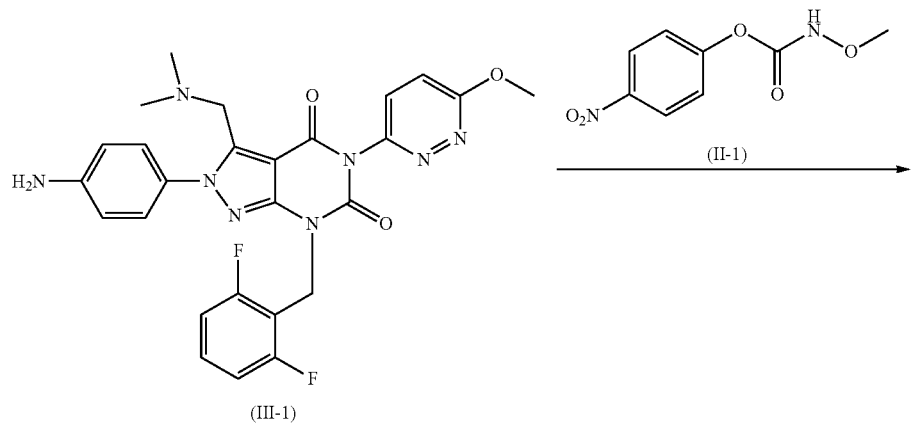

(III-1)

(II-1)

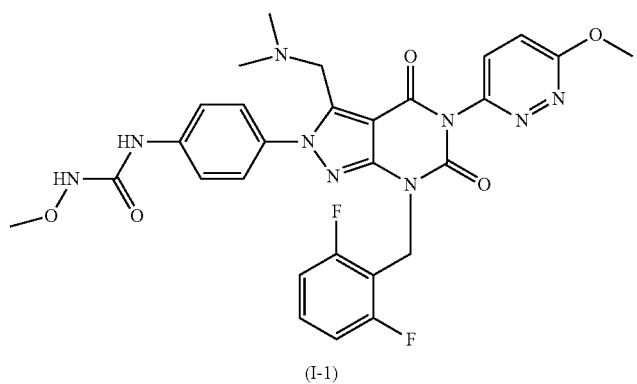

(I-1)

5. The method according to claim 4, wherein the compound of formula (III-1) is prepared by the following method:

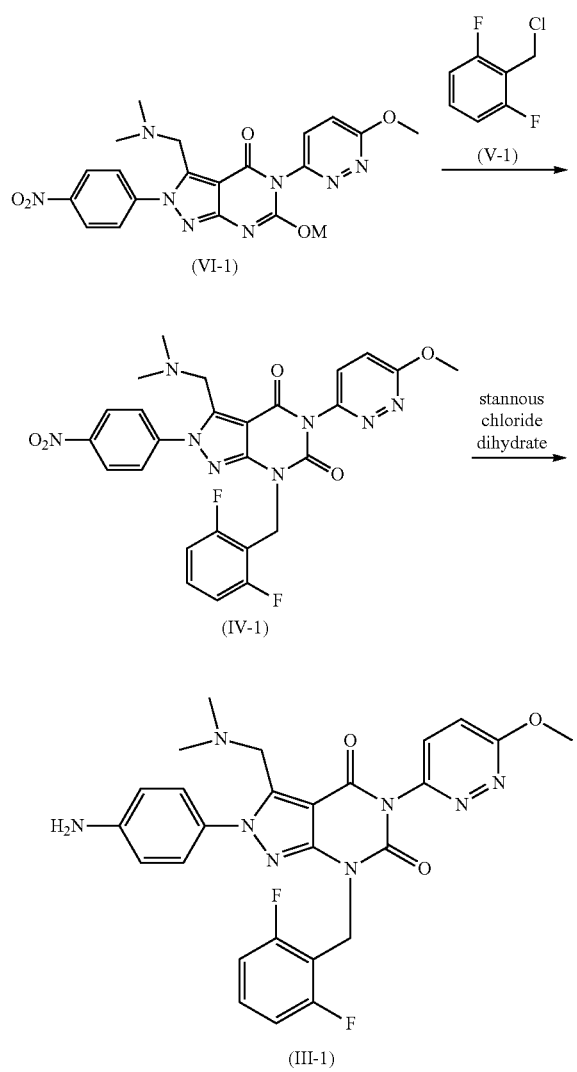

6. The method according to claim 5, wherein the compound of formula (VI-1) is prepared by the following method:

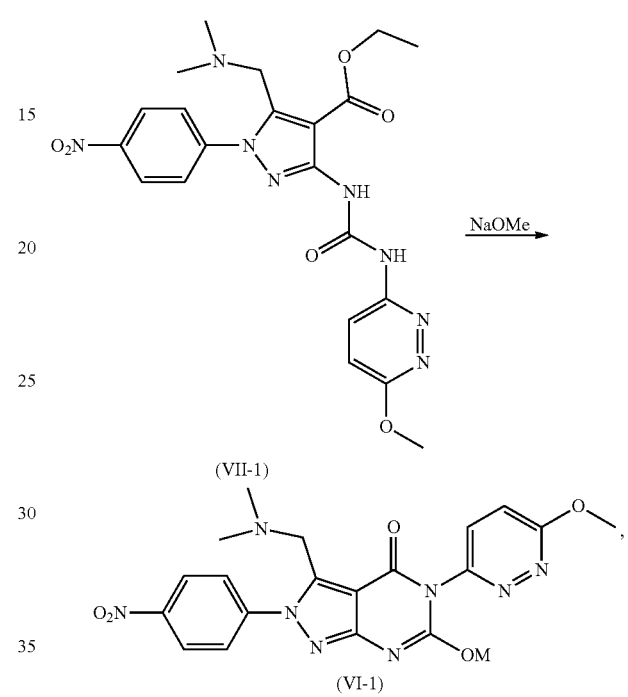

wherein the compound of formula (VI-1) is a mono-metal alkoxide or a bi-metal alkoxide; and M is selected from the group consisting of a monovalent metal cation, a divalent metal cation, a trivalent metal cation and a tetravalent metal cation.

wherein no acid is added in the post-treatment step of the method for preparing the compound of formula (VI-1) from the compound of formula (VII-1), and the acid is selected from the group consisting of an organic acid and an inorganic acid.

7. A method for preparing a compound of formula (I-1), wherein the method comprises

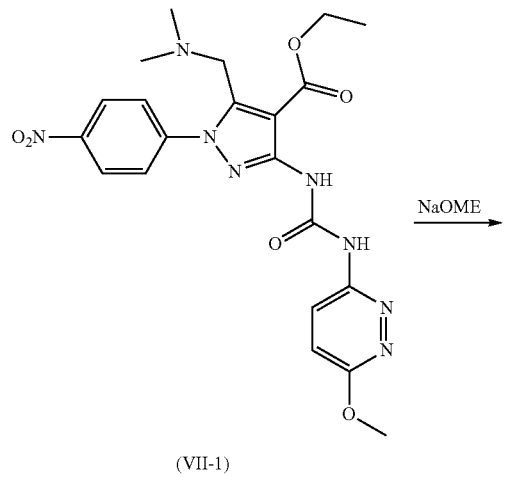

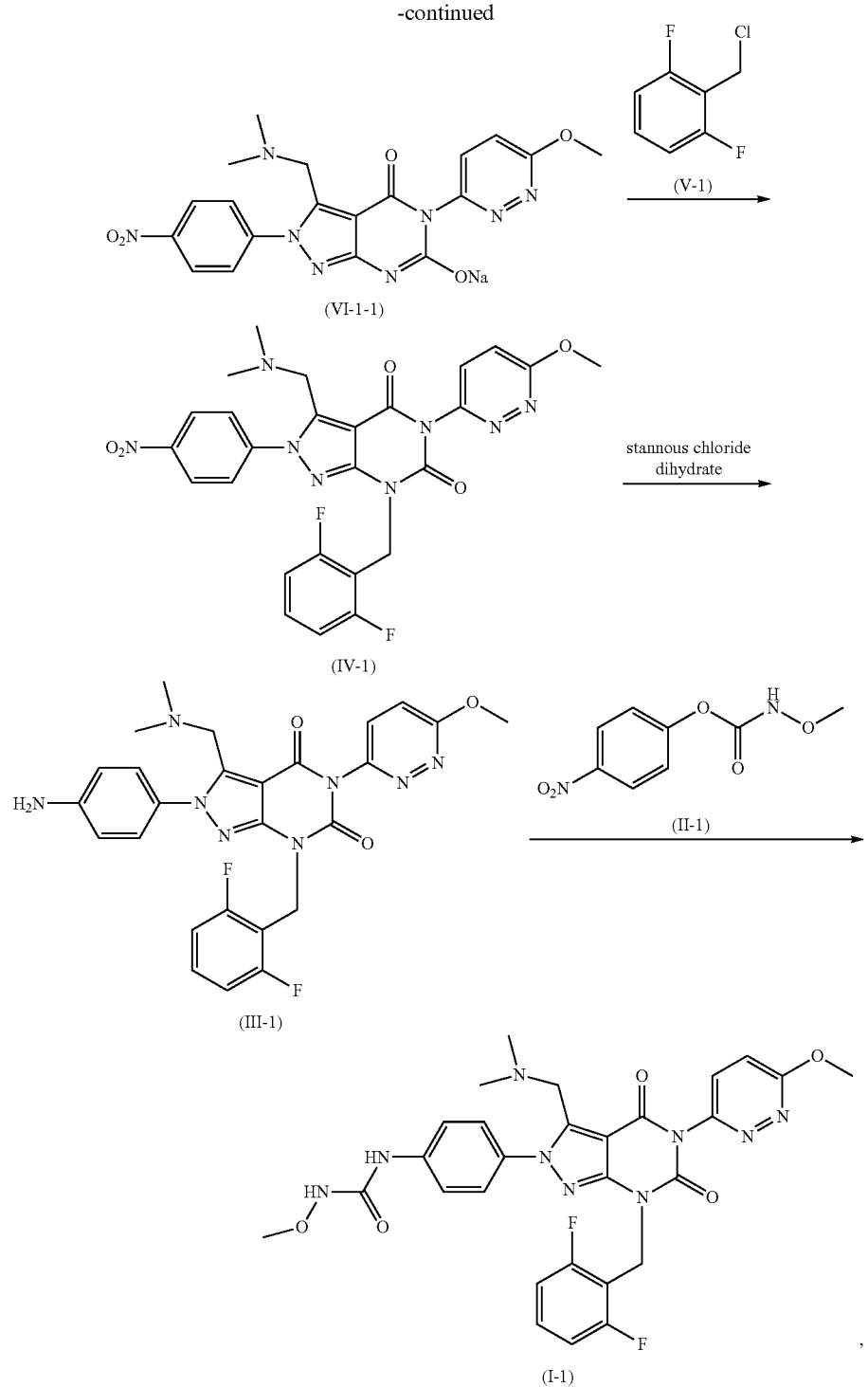
wherein no acid is added in the post-treatment step of preparing the compound of formula (VI-1-1) from the compound of formula (VII-1), and the acid is selected from the group consisting of an organic acid and an inorganic acid.
* * * * *